United States Patent
Castelhano et al.

(10) Patent No.: US 7,439,256 B2
(45) Date of Patent: Oct. 21, 2008

(54) (ARYLAMIDOARYL) CYANOGUANIDINE COMPOUNDS

(76) Inventors: Arlindo Castelhano, 1 Bioscience Park Dr., Farmingdale, NY (US) 11735; Andrew Crew, 1 Bioscience Park Dr., Farmingdale, NY (US) 11735; Hanqing Dong, 1 Bioscience Park Dr., Farmingdale, NY (US) 11735; An-Hu Li, 1 Bioscience Park Dr., Farmingdale, NY (US) 11735; Li Qiu, 1 Bioscience Park Dr., Farmingdale, NY (US) 11735; Alun Smith, Magnum Close, Streetly, Sutton Coldfield, Birmingham (GB) B74 2DN ( * ) Notice: Subject to any disclaimer, the term of this patent is extended or adjusted under 35 U.S.C. 154(b) by 48 days.

(21) Appl. No.: 11/227,346

(22) Filed: Sep. 15, 2005

(65) Prior Publication Data

US 2006/0074082 A1  Apr. 6, 2006

Related U.S. Application Data

(60) Provisional application No. 60/610,744, filed on Sep. 17, 2004.

(51) Int. Cl.
*A61K 31/47* (2006.01)
*C07D 453/02* (2006.01)

(52) U.S. Cl. ................. 514/314; 546/135
(58) Field of Classification Search ........... 546/135; 514/314

See application file for complete search history.

(56) References Cited

OTHER PUBLICATIONS

Tsuruo's, 1997, CAS: 127: 199501.*

* cited by examiner

*Primary Examiner*—Rei-Tsang Shiao

(57) ABSTRACT

Compounds represented by Formula (I):

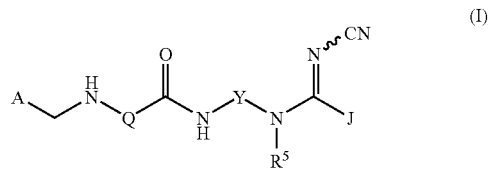

or a pharmaceutically acceptable salt or N-oxide thereof, wherein A, Q, Y, $R^5$ and J are defined herein, are useful in the treatment of cancer.

8 Claims, No Drawings

(ARYLAMIDOARYL) CYANOGUANIDINE COMPOUNDS

This application claims the benefit of U.S. Patent Application No. 60/610,744 filed 17 Sep. 2004.

BACKGROUND OF THE INVENTION

The present invention is directed to (arylamidoaryl)cyanoguanidines that are inhibitors of c-Kit proto-oncogene (also known as Kit, CD-117, stem cell factor receptor, mast cell growth factor receptor).

The c-Kit proto-oncogene is believed to be important in embryogenesis, melandgenesis, hematopoiesis, and the pathogenesis of mastocytosis, gastrointestinal tumors, and other solid tumors, as well as certain leukemias, including AML. Accordingly, it would be desirable to develop novel compounds that are inhibitors of the c-Kit receptor.

Many of the current treatment regimes for hyperproliferative disorders (cancer) utilize compounds that inhibit DNA synthesis. Such compounds' mechanism of operation is to be toxic to cells, particularly to rapidly dividing tumor cells. Thus, their broad toxicity can be a problem to the subject patient. However, other approaches to anti-cancer agents that act other than by the inhibition of DNA synthesis have been explored to try to enhance the selectivity of the anti-cancer action and thereby reduce adverse side-effects.

It is known that a cell may become cancerous by virtue of the transformation of a portion of its DNA into an oncogene (i.e. a gene which, on activation, leads to the formation of malignant tumor cells). Many oncogenes encode proteins that are aberrant protein-tyrosine kinases capable of causing cell transformation. By a different route, the overexpression of a normal proto-oncogenic tyrosine kinase can also result in proliferative disorders, sometimes resulting in a malignant phenotype. Alternatively, co-expression of a receptor tyrosine kinase and its cognate ligand within the same cell type may also lead to malignant transformation.

Receptor tyrosine kinases are large enzymes which span the cell membrane and possess i) an extracellular binding domain for growth factors such as KIT ligand (also known as stem cell factor (SCF), Steel factor (SLF) or mast cell growth factor (MGF)), ii) a transmembrane domain, and iii) an intracellular portion which functions as a kinase to phosphorylate specific tyrosine residues in proteins. Binding of KIT ligand to KIT tyrosine kinase results in receptor homodimerization, the activation of KIT tyrosine kinase activity, and the subsequent phosphorylation of a variety of protein substrates, many of which are effectors of intracellular signal transduction, These events can lead to enhanced cell proliferation or promote enhanced cell survival. With some receptor kinases, receptor heterodimerization can also occur.

It is known that such kinases are frequently aberrantly expressed in common human cancers such as breast cancer, head and neck cancers, gastrointestinal cancer such as colon, rectal or stomach cancer, leukemia, and ovarian, bronchial, lung or pancreatic cancer. Kit kinase expression has been documented in a wide variety of human malignancies such as mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma. The kinase activity of KIT has been implicated in the pathophysiology of several of these—and additional tumors—including breast carcinoma, SCLC, GIST, germ cell tumors, mast cell leukemia, neuroblastoma, AML, melanoma and ovarian carcinoma.

Several mechanisms of KIT activation in tumor cells have been reported, including activating mutations, autocrine and paracrine activation of the receptor kinase by its ligand, loss of protein-tyrosine phosphatase activity, and cross activation by other kinases. The transforming mechanisms initiated by the activating mutations are thought to include dimer formation and increased intrinsic activity of the kinase domain, both of which result in constitutive ligand-independent kinase activation, and possibly altered substrate specificity. More than thirty activating mutations of the Kit protein have been associated with highly malignant tumors in humans.

Accordingly, it has been recognized that inhibitors of receptor tyrosine kinases are useful as selective inhibitors of the growth of mammalian cancer cells. For example, Gleevec™ (also known as imatinib mesylate, or STI571), a 2-phenylpyrimidine tyrosine kinase inhibitor that inhibits the kinase activity of the BCR-ABL fusion gene product, was recently approved by the U.S. Food and Drug Administration for the treatment of CML. Gleevec™, in addition to inhibiting BCR-ABL kinase, also inhibits the KIT kinase and PDGF receptor kinase, although it is not effective against all mutant isoforms of the KIT kinase. Kit ligand-stimulated growth of MO7e human leukemia cells is inhibited by Gleevec™, which also induces apoptosis under these conditions. By contrast, GM-CSF stimulated growth of MO7e human leukemia cells is not affected by Gleevec™. Further, in recent clinical studies using Gleevec™ to treat patients with GIST, a disease in which KIT kinase is involved in transformation of the cells, many of the patients showed marked improvement.

These studies demonstrate how KIT kinase inhibitors can treat tumors whose growth is dependent on KIT kinase activity. Other kinase inhibitors show even greater kinase selectivity. For example, the 4-anilinoquinazoline compound Tarceva™ inhibits only EGF receptor kinase with high potency, although it can inhibit the signal transduction of other receptor kinases, probably by virtue of the fact that these receptors heterodimerize with EGF receptor.

Although anti-cancer compounds such as those described above make a significant contribution to the art, there is a continuing need for improved anti-cancer pharmaceuticals, and it would be desirable to develop new compounds with better selectivity or potency, or with reduced toxicity or side effects.

International Patent Publication No. WO99/32433 describes thiourea and benzamide compounds. International Patent Publication No. WO03/037274 describes pyrazoleamides and pyrazole-sulfonamides. U.S. Pat. No. 5,541,343 describes cyclic imino derivatives.

International Patent Publication No. WO02/42265 describes cyanoguanidine prodrugs. International Patent Publication No. WO00/61559 describes N-substituted cyanoguanidine compounds. U.S. Pat. No. 6,054,457 describes benzamide derivatives.

SUMMARY OF THE INVENTION

Compounds represented by Formula (I):

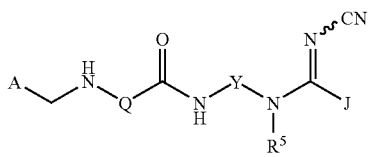

(I)

or a pharmaceutically acceptable salt or N-oxide thereof. The compounds of Formula (I) are useful in the treatment of tumors and cancers such as mastocytosis/mast cell leukemia, gastrointestinal stromal tumors (GIST), germ cell tumors, small cell lung carcinoma (SCLC), sinonasal natural killer/T-cell lymphoma, testicular cancer (sentinoma), thyroid carcinoma, malignant melanoma, ovarian carcinoma, adenoid cystic carcinoma, acute myelogenous leukemia (AML), breast carcinoma, pediatric T-cell acute lymphoblastic leukemia, neuroblastoma, mast cell leukemia, angiosarcoma, anaplastic large cell lymphoma, endometrial carcinoma, and prostate carcinoma.

DETAILED DESCRIPTION OF THE INVENTION

The present invention is directed to a compound represented by Formula (I):

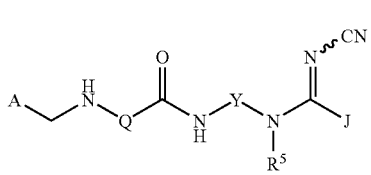

(I)

or a pharmaceutically acceptable salt or N-oxide thereof, wherein:

Q is heteroaryl optionally substituted with 1-2 independent $R^3$ substituents;

Y is aryl or heteroaryl, either of which is optionally substituted with 1-4 independent $R^{31}$ substituents;

J is $-NR^1R^2$, $-OR^1$, or $-SR^1$;

A is aryl, heteroaryl, cyclo$C_{3-10}$alkyl, heterocyclyl, cyclo$C_{3-10}$alkenyl, or heterocycloalkenyl, each of which is optionally substituted by 1-5 independent $R^4$ substituents;

$R^1$ and $R^2$ are $C_{0-6}$alkyl, aryl, heteroaryl, cyclo$C_{3-10}$alkyl, heterocyclyl, cyclo$C_{3-10}$alkenyl, heterocycloalkenyl, $C_{2-6}$alkenyl, $C_{2-6}$alkynyl, each of which is optionally substituted by 1-5 independent $R^{41}$ substituents; provided that neither $R^1$ nor $R^2$ is pyridyl;

or $R^1$ and $R^2$, taken together with the N atom to which they are attached, form a heterocyclyl, heterocycloalkenyl, or heteroaryl, each of which is optionally substituted with 1-4 independent $R^{41}$ substituents;

$R^3$ and $R^{31}$ each independently is $C_{0-6}$alkyl, cyclo$C_{3-10}$alkyl, haloalkyl, halogen, cyano$C_{0-6}$alkyl, nitro$C_{0-6}$alkyl, hydroxy$C_{0-6}$alkyl, $C_{0-6}$alkylamino$C_{0-6}$alkyl, acyl$C_{0-6}$alkyl, substituted acyl, acylamino$C_{0-6}$alkyl, substituted acylamino, acyloxy$C_{0-6}$alkyl, substituted acyloxy, ar$C_{0-6}$alkyl, heteroaryl$C_{0-6}$alkyl, arylhydrazino, alkylsulfonamido$C_{0-6}$alkyl, arylsulfonamido$C_{0-6}$alkyl, alkylsulfonyl$C_{0-6}$alkyl, arylsulfonyl$C_{0-6}$alkyl, alkylsulfinyl$C_{0-6}$alkyl, heterocyclylsulfonyl$C_{0-6}$ alkyl, silyl, siloxy$C_{0-6}$alkyl, alkenoxy$C_{0-6}$alkyl, alkynoxy$C_{0-6}$alkyl, $C_{1-6}$alkoxy$C_{0-6}$alkyl, $C_{1-6}$alkylthio$C_{0-6}$ alkyl, $C_{2-6}$alkenyl, acyl$C_{2-6}$alkenyl, $C_{2-6}$alkynyl, acyl$C_{2-6}$alkynyl, ar$C_{0-6}$alkylamino$C_{0-6}$alkyl, ar$C_{0-6}$alkylthio$C_{0-6}$ alkyl, ar$C_{0-6}$alkoxy$C_{0-6}$alkyl, substituted ar$C_{0-6}$alkoxy, substituted ar$C_{0-6}$alkylthio, or substituted ar$C_{0-6}$alkoxy;

$R^4$ and $R^{41}$ each independently is $C_{0-6}$alkyl, cyclo$C_{3-10}$ alkyl, oxo, halogen, haloalkyl, cyano$C_{0-6}$alkyl, nitro$C_{0-6}$ alkyl, hydroxy$C_{0-6}$alkyl, $(C_{0-6}$alkyl)$(C_{0-6}$alkyl)amino$C_{0-6}$ alkyl, $(C_{0-6}$alkyl)$(C_{0-6}$alkyl)amino$(C_{1-6}$alkyl)amino$C_{0-6}$ alkyl, acylamino$C_{0-6}$alkylamino, acyl$C_{0-6}$alkyl, $(C_{0-6}$alkyl)$(C_{0-6}$alkyl)aminoacyl, substituted acyl, guanidino$C_{0-6}$alkyl, hydroxyimino$C_{0-6}$alkyl, acylamino$C_{0-6}$alkyl, optionally substituted acylamino, optionally substituted acyloxy$C_{0-6}$alkyl, optionally substituted ar$C_{0-6}$alkyl, optionally substituted heteroaryl$C_{0-6}$alkyl, optionally substituted heterocyclyl$C_{0-6}$ alkyl, cyanoamino$C_{0-6}$alkyl, $C_{0-6}$alkylhydrazino, heterocyclylamino, ar$C_{0-6}$alkylhydrazino, alkylsulfonyl$C_{0-6}$alkyl, ar$C_{0-6}$alkylsulfonyl$C_{0-6}$alkyl, alkylsulfinyl$C_{0-6}$alkyl, alkylsulfonamido$C_{0-6}$alkyl, ar$C_{0-6}$alkylsulfonamido$C_{0-6}$alkyl, amino$C_{0-6}$alkylsulfonyl, $C_{0-6}$alkylaminosulfonyl, acyl$C_{1-6}$ alkylsulfonyl, heterocyclylsulfonyl, amino$C_{0-6}$alkylsulfinyl, acyl$C_{1-6}$alkylsulfinyl, silyl, siloxy, alkenoxy, alkynoxy, $C_{2-6}$alkenyl, acyl$C_{2-6}$alkenyl, $C_{2-6}$alkynyl, acyl$C_{2-6}$alkynyl, hydroxy$C_{2-6}$alkynyl, amino$C_{2-6}$alkynyl, $C_{1-6}$alkoxy$C_{0-6}$ alkyl, $C_{1-6}$alkylthio$C_{0-6}$alkyl, hydroxy$C_{1-6}$alkoxy$C_{0-6}$alkyl, hydroxy$C_{1-6}$alkylthio$C_{0-6}$alkyl, acyl$C_{1-6}$alkoxy$C_{0-6}$alkyl, acyl$C_{1-6}$alkylthio$C_{0-6}$alkyl, $C_{0-6}$alkylamino$C_{1-6}$alkoxy$C_{0-6}$ alkyl, $C_{0-6}$alkylamino$C_{1-6}$alkylthio$C_{0-6}$alkyl, acylamino$C_{1-6}$ alkoxy$C_{0-6}$alkyl, acylamino$C_{1-6}$alkylthio$C_{0-6}$alkyl, ar$C_{0-6}$ alkylamino$C_{0-6}$alkyl, ar$C_{0-6}$alkylthio$C_{0-6}$alkyl, ar$C_{0-6}$ alkoxy$C_{0-6}$alkyl, ar$C_{0-6}$alkylamino, ar$C_{0-6}$alkylamino$C_{0-6}$ alkyl, ar$C_{0-6}$alkylthio, optionally substituted ar$C_{0-6}$alkoxy, optionally substituted ar$C_{0-6}$alkylthio, or optionally substituted ar$C_{0-6}$alkoxy;

$R^5$ is $C_{0-6}$alkyl, $C_{1-6}$alkoxy$C_{1-6}$alkyl, $C_{1-6}$alkylthio$C_{1-6}$ alkyl, $C_{0-6}$alkylamino$C_{1-6}$alkyl, ar$C_{0-6}$alkyl; or $R^5$ is a bridge between the N atom to which it is attached and one of the C ring atoms of Y, thereby forming a bicyclic heteroaryl group; and provided that the compound is not 2,2,2-trifluoroethyl N'-cyano-N-{4-[({3-[(quinolin-4-ylmethyl)amino]thien-2-yl}carbonyl)amino]phenyl}-imidocarbamate;

2,2,2-trifluoroethyl N-{2-chloro-5-[({3-[(quinolin-4-ylmethyl)amino]thien-2-yl}carbonyl)amino]phenyl}-N-cyanoimidocarbamate; or N-{1-[(cyanoimino)(dimethylamino)methyl]-2,3-dihydro-1H-indol-6-yl}-3-((quinolin-4-ylmethyl)amino) thiophene-2-carboxamide.

In one aspect, the present invention is directed to a compound represented by Formula (I), or a pharmaceutically acceptable salt or N-oxide thereof, wherein J is —NR¹R²; and the other variables are as described above for Formula (I).

In an embodiment of this one aspect, the present invention is directed to a compound represented by Formula (I), or a pharmaceutically acceptable salt or N-oxide thereof, wherein J is —NR¹R²; Y is aryl optionally substituted with 1-4 independent R³¹ substituents; and the other variables are as described above for Formula (I).

In another embodiment of this one aspect, the present invention is directed to a compound represented by Formula (I), or a pharmaceutically acceptable salt or N-oxide thereof, wherein J is —NR¹R²; Y is aryl optionally substituted with 1-4 independent R³¹ substituents; Q is thienyl optionally substituted with 1-2 independent R³ substituents; and the other variables are as described above for Formula (I).

In yet another embodiment of this one aspect, the present invention is directed to a compound represented by Formula (I), or a pharmaceutically acceptable salt or N-oxide thereof, wherein J is —NR¹R²; Y is aryl optionally substituted with 1-4 independent R³¹ substituents; Q is thienyl optionally substituted with 1-2 independent R³ substituents; A is heteroaryl optionally substituted by 1-5 independent R⁴ substituents; and the other variables are as described above for Formula (I).

In still another embodiment of this one aspect, the present invention is directed to a compound represented by Formula (I), or a pharmaceutically acceptable salt or N-oxide thereof, wherein J is —NR¹R²; Y is

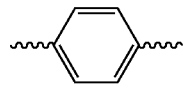

optionally substituted with 1-4 independent R³¹ substituents; and the other variables are as described above for Formula (I).

In another embodiment of this one aspect, the present invention is directed to a compound represented by Formula (I), or a pharmaceutically acceptable salt or N-oxide thereof, wherein J is —NR¹R²; Y is

optionally substituted with 1-4 independent R³¹ substituents; Q is thienyl optionally substituted with 1-2 independent R³ substituents; and the other variables are as described above for Formula (I).

In yet still another embodiment of this one aspect, the present invention is directed to a compound represented by Formula (I), or a pharmaceutically acceptable salt or N-oxide thereof, wherein J is —NR¹R²; Y is

optionally substituted with 1-4 independent R³¹ substituents; wherein Q is thienyl optionally substituted with 1-2 independent R³ substituents; A is heteroaryl optionally substituted by 1-5 independent R⁴ substituents; and the other variables are as described above for Formula (I).

In still another embodiment of this one aspect, the present invention is directed to a compound represented by Formula (I), or a pharmaceutically acceptable salt or N-oxide thereof, wherein J is —NR¹R²; R⁵ is a bridge between the N atom to which it is attached and one of the C ring atoms of Y, forming an indole; and the other variables are as described above for Formula (I).

In yet another embodiment of this one aspect, the present invention is directed to a compound represented by Formula (I), or a pharmaceutically acceptable salt or N-oxide thereof, wherein J is —NR¹R²; R⁵ is a bridge between the N atom to which it is attached and one of the C ring atoms of Y, forming an indole; Q is thienyl optionally substituted with 1-2 independent R³ substituents; and the other variables are as described above for Formula (I).

In another embodiment of this one aspect, the present invention is directed to a compound represented by Formula (I), or a pharmaceutically acceptable salt or N-oxide thereof, wherein J is —NR¹R²; R⁵ is a bridge between the N atom to which it is attached and one of the C ring atoms of Y, forming an indole; Q is thienyl optionally substituted with 1-2 independent R³ substituents; A is heteroaryl optionally substituted by 1-5 independent R⁴ substituents; and the other variables are as described above for Formula (I).

In a second aspect, the present invention is directed to a compound represented by Formula (I), or a pharmaceutically acceptable salt or N-oxide thereof, wherein J is —OR¹ or —SR¹; and the other variables are as described above for Formula (I).

In an embodiment of this second aspect, the present invention is directed to a compound represented by Formula (I), or a pharmaceutically acceptable salt or N-oxide thereof, wherein J is —OR¹ or —SR¹; Y is aryl optionally substituted with 1-4 independent R³¹ substituents; and the other variables are as described above for Formula (I).

In another embodiment of this second aspect, the present invention is directed to a compound represented by Formula (I), or a pharmaceutically acceptable salt or N-oxide thereof, wherein J is —OR¹ or —SR¹; Y is aryl optionally substituted with 1-4 independent R³¹ substituents; Q is thienyl optionally substituted with 1-2 independent R³ substituents; and the other variables are as described above for Formula (I).

In yet another embodiment of this second aspect, the present invention is directed to a compound represented by Formula (I), or a pharmaceutically acceptable salt or N-oxide thereof, wherein J is —OR¹ or —SR¹; Y is aryl optionally substituted with 1-4 independent R³¹ substituents; Q is thienyl optionally substituted with 1-2 independent R³ substituents; A is heteroaryl optionally substituted by 1-5 independent R⁴ substituents; and the other variables are as described above for Formula (I).

The present invention includes the following compounds:
phenyl N'-cyano-N-{3-[({3-[(quinolin-4-ylmethyl)amino]thien-2-yl}carbonyl)amino]phenyl}-imidocarbamate;

N-(3-{[(cyanoimino)(morpholin-4-yl)methyl]amino}phenyl)-3-((quinolin-4-ylmethyl)amino)thiophene-2-carboxamide;

2,2,2-trifluoroethyl N'-cyano-N-{3-[({3-[(quinolin-4-ylmethyl)amino]thien-2-yl}carbonyl)amino]phenyl}-imidocarbamate;

N-(3-{[(cyanoimino)(methylamino)-methyl]amino}phenyl)-3-((quinolin-4-ylmethyl)amino)thiophene-2-carboxamide;

N-(3-{[(cyanoimino)(4-methylpiperazin-1-yl)methyl]amino}phenyl)-3-((quinolin-4-ylmethyl)amino)thiophene-2-carboxamide;

N-(3-{[(cyanoimino)(2-methoxyethylamino)methyl]-amino}phenyl)-3-((quinolin-4-ylmethyl)amino)thiophene-2-carboxamide;

N-(3-{[(cyanoimino)(2-(dimethylamino)ethylamino)-methyl]amino}phenyl)-3-((quinolin-4-ylmethyl)amino)thiophene-2-carboxamide;

N-(3-{[(cyanoimino)(piperazin-1-yl)methyl]amino}phenyl)-3-((quinolin-4-ylmethyl)amino)thiophene-2-carboxamide;

N-(3-{[(cyanoimino)(3-hydroxypyrrolidin-1-yl)methyl]amino}phenyl)-3-((quinolin-4-ylmethyl)amino)thiophene-2-carboxamide;

N-(3-{[(cyanoimino)(2-morpholine-4-ylethylamino)methyl]amino}-phenyl)-3-((quinolin-4-ylmethyl)amino)thiophene-2-carboxamide;

N-(3-{[(cyanoimino)(3-(1H-imidazolyl)propylamino)methyl]-amino}phenyl)-3-((quinolin-4-ylmethyl)amino)thiophene-2-carboxamide;

N-(3-{[(cyanoimino)(piperidin-1-yl)methyl]amino}phenyl)-3-((quinolin-4-ylmethyl)amino)thiophene-2-carboxamide;

N-(3-{[(cyanoimino)(2-piperidine-1-ylethylamino)methyl]amino}-phenyl)-3-((quinolin-4-ylmethyl)amino)thiophene-2-carboxamide;

N-(3-{[(cyanoimino)(dimethylamino)-methyl]amino}phenyl)-3-((quinolin-4-ylmethyl)amino)thiophene-2-carboxamide;

N-(3-{[(cyanoimino)(4-hydroxypiperidin-1-yl)methyl]amino}phenyl)-3-((quinolin-4-ylmethyl)amino)thiophene-2-carboxamide;

N-(3-{[(cyanoimino)(cyclohexylamino)methyl]amino}phenyl)-3-((quinolin-4-ylmethyl)amino)thiophene-2-carboxamide;

N-(3-{[(cyanoimino)(2-(1-methylpyrrolidin-2-yl)ethylamino)methyl]amino}-phenyl)-3-((quinolin-4-ylmethyl)amino)thiophene-2-carboxamide;

N-(3-{[(cyanoimino)(pyridine-3-ylmethylamino)methyl]amino}-phenyl)-3-((quinolin-4-ylmethyl)amino)thiophene-2-carboxamide;

N-(3-{[amino(cyanoimino)methyl]-amino}phenyl)-3-((quinolin-4-ylmethyl)amino)thiophene-2-carboxamide;

N-(3-{[(cyanoimino)(bis(2-methoxyethyl)amino)methyl]-amino}phenyl)-3-((quinolin-4-ylmethyl)amino)thiophene-2-carboxamide;

N-(4-{[(cyanoimino)(dimethylamino)-methyl]amino}phenyl)-3-((quinolin-4-ylmethyl)amino)thiophene-2-carboxamide;

N-(4-{[(cyanoimino)(morpholin-4-yl)methyl]amino}phenyl)-3-((quinolin-4-ylmethyl)amino)thiophene-2-carboxamide;

N-(4-{[amino(cyanoimino)methyl]-amino}phenyl)-3-((quinolin-4-ylmethyl)amino)thiophene-2-carboxamide;

N-(4-{[(cyanoimino)(methylamino)-methyl]amino}phenyl)-3-((quinolin-4-ylmethyl)amino)thiophene-2-carboxamide;

N-(4-{[(cyanoimino)(2-methoxyethylamino)methyl]-amino}phenyl)-3-((quinolin-4-ylmethyl)amino)thiophene-2-carboxamide;

Phenyl N-[2-chloro-5-({[3-((quinolin-4-ylmethyl)amino)thien-2-yl]carbonyl}amino)phenyl]-N'-cyanoimidocarbamate;

N-(3-{[amino(cyanoimino)methyl]-amino}5-chlorophenyl)-3-((quinolin-4-ylmethyl)amino)thiophene-2-carboxamide;

N-(3-{[(cyanoimino)(dimethylamino)-methyl]amino}-5-chlorophenyl)-3-((quinolin-4-ylmethyl)amino)thiophene-2-carboxamide;

N-(3-{[(cyanoimino)(2-methoxyethylamino)methyl]-amino}-5-chlorophenyl)-3-((quinolin-4-ylmethyl)amino)thiophene-2-carboxamide;

N-(3-{[amino(cyanoimino)methyl]-amino}-5-trifluoromethylphenyl)-3-((quinolin-4-ylmethyl)amino)thiophene-2-carboxamide;

N-(3-{[(cyanoimino)(dimethylamino)-methyl]ammo}-5-trifluoromethylphenyl)-3-((quinolin-4-ylmethyl)amino)thiophene-2-carboxamide;

N-(3-{[(cyanoimino)(2-methoxyethylamino)methyl]-amino}-5-trifluoromethylphenyl)-3-((quinolin-4-ylmethyl)amino)thiophene-2-carboxamide;

N-(3-{[(cyanoimino)(methylamino)-methyl]amino}-5-chlorophenyl)-3-((quinolin-4-ylmethyl)amino)thiophene-2-carboxamide;

N-(3-{[(cyanoimino)(2-(dimethylamino)ethylamino)-methyl]amino}-5-chlorophenyl)-3-((quinolin-4-ylmethyl)amino)thiophene-2-carboxamide;

N-(3-{[(cyanoimino)(2-morpholine-4-ylethylamino)methyl]amino}-5-chlorophenyl)-3-((quinolin-4-ylmethyl)amino)thiophene-2-carboxamide;

N-(3-{[(cyanoimino)(2-(dimethylamino)ethylamino)-methyl]amino}-5-trifluoromethylphenyl)-3-((quinolin-4-ylmethyl)amino)thiophene-2-carboxamide;

N-(3-{[(cyanoimino)(2-morpholine-4-ylethylamino)methyl]amino}-5-trifluoromethylphenyl)-3-((quinolin-4-ylmethyl)amino)thiophene-2-carboxamide;

N-(3-{[(cyanoimino)(2-morpholine-4-yl)methyl]amino}-5-trifluoromethylphenyl)-3-((quinolin-4-ylmethyl)amino)thiophene-2-carboxamide;

N-(3-{[(cyanoimino)(4-methylpiperazin-1-yl)methyl]amino}-5-trifluoromethylphenyl)-3-((quinolin-4-ylmethyl)amino)thiophene-2-carboxamide;

N-(3-{[(cyanoimino)(3-hydroxypyrrolidin-1-yl)methyl]amino}-5-trifluoromethylphenyl)-3-((quinolin-4-ylmethyl)amino)thiophene-2-carboxamide;

N-(3-{[(cyanoimino)(3-(1H-imidazolyl)propylamino)methyl]-amino}-5-trifluoromethylphenyl)-3-((quinolin-4-ylmethyl)amino)thiophene-2-carboxamide;

(2R)-1-[{[3-{[(3-((quinolin-4-ylmethyl)amino)thien-2-yl)carbonyl]amino}-5-(trifluoromethyl)phenyl]amino}-(cyanoimino)methyl]pyrrolidine-2-carboxamide;

N-(3-{[(cyanoimino)(pyridine-3-ylmethylamino)methyl]amino}-5-trifluoromethylphenyl)-3-((quinolin-4-ylmethyl)amino)thiophene-2-carboxamide;

N-(3-{[(cyanoimino)(methylamino)-methyl]amino}-5-trifluoromethylphenyl)-3-((quinolin-4-ylmethyl)amino)thiophene-2-carboxamide;

2,2,2-trifluoroethyl N'-cyano-N-{2-methyl-5-[({3-[(quinolin-4-ylmethyl)amino]thien-2-yl}carbonyl)amino]phenyl}-imidocarbamate;

N-(3-{[(cyanoimino)(methylamino)-methyl]amino}-4-methylphenyl)-3-((quinolin-4-ylmethyl)amino)thiophene-2-carboxamide;

N-(3-{[(cyanoimino)(dimethylamino)-methyl]amino}-4-methylphenyl)-3-((quinolin-4-ylmethyl)amino)thiophene-2-carboxamide;

N-(3-{[(cyanoimino)(2-methoxyethylamino)methyl]-amino}4-methylphenyl)-3-((quinolin-4-ylmethyl)amino)thiophene-2-carboxamide;

(2R)-1-[{[3-{[(3-((quinolin-4-ylmethyl)amino)thien-2-yl)carbonyl]amino}phenyl]amino}(cyanoimino)methyl]pyrrolidine-2-carboxamide;

(2S)-1-[{[3-{[(3-((quinolin-4-ylmethyl)amino)thien-2-yl)carbonyl]amino}phenyl]amino}(cyanoimino)methyl]pyrrolidine-2-carboxamide;

Phenyl N-cyano-6-({[3-((quinolin-4-ylmethyl)amino)thien-2-yl]carbonyl}amino)indoline-1-carboximidoate;

N-{1-[(cyanoimino)(methylamino)methyl]-2,3-dihydro-1H-indol-6-yl}-3-((quinolin-4-ylmethyl)amino)thiophene-2-carboxamide;

N-{1-[(cyanoimino)(2-methoxyethylamino)methyl]-2,3-dihydro-1H-indol-6-yl}-3-((quinolin-4-ylmethyl)amino)thiophene-2-carboxamide;

N-{1-[(cyanoimino)(4-methylpiperazin-1-yl)methyl]-2,3-dihydro-1H-indol-6-yl}-3-((quinolin-4-ylmethyl)amino)thiophene-2-carboxamide;

N-{1-[(cyanoimino)(pyrrolidin-1-yl)methyl]-2,3-dihydro-1H-indol-6-yl}-3-((quinolin-4-ylmethyl)amino)thiophene-2-carboxamide;

N-{1-[amino(cyanoimino)methyl]-2,3-dihydro-1H-indol-6-yl}-3-[(quinolin-4-ylmethyl)amino]thiophene-2-carboxamide;

N-{1-[(cyanoimino)(2-morpholine-4-yl)methyl]-2,3-dihydro-1H-indol-6-yl}-3-((quinolin-4-ylmethyl)amino)thiophene-2-carboxamide or a pharmaceutically acceptable salt, or N-oxide, thereof.

The present invention is also directed to a method of treating hyperproliferative disorders, including breast cancer, head cancer, or neck cancer, gastrointestinal cancer, leukemia, ovarian, bronchial, lung, or pancreatic cancer, sinonasal natural killer/T-cell lymphoma, testicular cancer (seminoma), thyroid carcinoma, malignant melanoma, adenoid cystic carcinoma, angiosarcoma, anaplastic large cell lymphoma, endometrial carcinoma, or prostate carcinoma, by administering an effective amount of a compound represented by Formula (I), or a pharmaceutically acceptable salt thereof.

In the present invention, the cyano group pendent on the upper right shown in Formula (I) can be in the cis or trans configuration. The present invention includes both the cis and trans isomers.

As used herein, "$C_{0-6}$alkyl" is used to mean an alkyl having 0-6 carbons—that is, 0, 1, 2, 3, 4, 5, or 6 carbons in a straight or branched configuration. An alkyl having no carbon is hydrogen when the alkyl is a terminal group. An alkyl having no carbon is a direct bond when the alkyl is a bridging (connecting) group.

As used herein unless otherwise specified, "alkyl", "alkenyl", and "alkynyl" includes straight or branched configurations. Lower alkyls, alkenyls, and alkynyls have 1-6 carbons. Higher alkyls, alkenyls, and alkynyls have more than 6 carbons.

As used herein unless otherwise specified, "halogen" is fluorine, chlorine, bromine or iodine.

As used herein unless otherwise specified, "substituted" is used to mean having 1-5 independent $C_{0-6}$alkyl, halogen, nitro, cyano, haloalkyl, $C_{0-6}$alkoxy, $C_{0-6}$alkylthio, or $C_{0-6}$alkylamino substituents As used herein unless otherwise specified, "haloalkyl" includes alkyl groups substituted with one or more halogens, for example, chloromethyl, 2-bromoethyl, 3-iodopropyl, trifluoromethyl, perfluoropropyl, 8-chlorononyl, and the like.

As used herein unless otherwise specified, the terms "aryl" and "ar" are well known to chemists and include, for example, phenyl and naphthyl, as well as phenyl with one or more short alkyl groups (tolyl, xylyl, mesityl, cumenyl, di(t-butyl)phenyl). Phenyl, naphthyl, tolyl, and xylyl are preferred. "Substituted aryl" is an aryl substituted with suitable substituents such as, for example, acyl, substituted acyl, N-protected piperazinylsulfonyl, piperazinylsulfonyl, N—$C_{1-6}$alkylpiperazinylsulfonyl, hydroxy$C_{1-6}$alkyl, heterocyclyl, halogen, nitro, amino, $C_{1-6}$alkylamino, cyano, or $C_{1-6}$alkoxy.

As used herein unless otherwise specified, the term "cycloalkyl" is well known to chemists and includes cyclic aliphatic ring structures, optionally substituted with alkyl, hydroxyl, oxo, and halo, such as cyclopropyl, methylcyclopropyl, cyclobutyl, cyclopentyl, 2-hydroxycyclopentyl, cyclopentanonyl, cyclohexyl, 4-chlorocyclohexyl, cycloheptyl, cyclooctyl, and the like.

As used herein unless otherwise specified, the term "cycloalkyl" is well known to chemists and includes cyclic aliphatic ring structures having at least one ethylenic bond, optionally substituted with alkyl, hydroxyl, oxo, and halo, for example, methylcyclopropenyl, trifluoromethylcyclopropenyl, cyclopentenyl, cyclohexenonyl, cyclohexenyl, 1,4-cyclohexadienyl, and the like.

As used herein unless otherwise specified, "heterocyclyl" is well known to chemists and includes unsaturated, saturated, or partially saturated, mono or polycyclic heterocyclic groups containing at least one N, S or O hetero-ring atom such as, for example, tetrahydrofuranyl, tetrahydrofuryl, pyrrolidinyl, piperidinyl, tetrahydropyranyl, thiolanyl, morpholinyl, piperazinyl, homopiperazinyl, dioxolanyl, dioxanyl, indolinyl, or chromanyl and the like. Such heterocyclyls can be suitably substituted with lower alkyl or oxo substituents.

As used herein unless otherwise specified, "heteroaryl" is well known to chemists and includes partially saturated, mono or polycyclic heterocyclic groups containing at least one N, S or O hetero-ring atom such as, for example, pyrazolyl, pyridyl, pyrimidinyl, pyrazinyl, pyridazinyl, triazolyl, tetrazolyl, pyrrolidinyl, indolyl, indolinyl, isoindolyl, indolizinyl, benzimidazolyl, quinolyl, isoquinolyl, imidazopyridyl, indazolyl, benzotriazolyl, tetrazolo-pyridazinyl, pyranyl, furyl, thienyl, oxazolyl, isoxazolyl, oxazolyl, benzofuranyl, benzoxazolyl, benzoxadiazolyl, thiazolyl, thiadiazolyl, thiazolidinyl, benzothiazolyl, benzothiadiazolyl, benzofuranyl, or benzodioxyl, imidazolyl, pyrrolyl, oxadiazolyl, quinolyl, benzotriazolyl, or benzothienyl and the like. Such heterocyclyls can be suitably substituted with lower alkyl or oxo substituents.

As used herein unless otherwise specified, "heterocycloalkenyl" includes mono or polycyclic heterocyclic groups having at least one ethylenic bond and containing at least one N, S or O hetero-ring atom such as, for example, dihydropyranyl, dihydrofuran, pyrrolinyl or the like. Such heterocycloalkenyls can be suitably substituted with lower alkyl or oxo substituents.

As used herein unless otherwise specified, "acyl" includes for example, carboxy, esterified carboxy, carbamoyl, lower alkylcarbamoyl, lower alkanoyl, aroyl, heterocyclylcarbonyl, and the like. Esterified carboxy includes substituted or unsubstituted lower alkoxycarbonyl such as methoxycarbonyl, ethoxycarbonyl, propoxycarbonyl, butoxycarbonyl, t-butoxycarbonyl, hexyloxycarbonyl, 2-iodoethoxycarbonyl, 2,2,2-trichloroethoxycarbonyl, dimethylaminopropoxycarbonyl, dimethylaminoethoxycarbonyl; substituted or unsubstituted aryloxycarbonyl such as phenoxycarbonyl, 4-nitrophenoxycarbonyl, 2-naphthyloxycarbonyl; substituted or unsubstituted ar(lower)alkoxycarbonyl such as benzyloxycarbonyl, phenethyloxycarbonyl, benzhydryloxycarbonyl, 4-nitrobenzyloxycarbonyl, 3-methoxy-4-nitrobenzyloxycarbonyl; and N-containing heterocyclyloxycarbonyl such as N-methylpiperidyloxycarbonyl and the like.

As used herein unless otherwise specified, "$C_{0-6}$alkylhydrazino" may be 2-mono or 2,2-di($C_{0-6}$alkyl)hydrazino such as 2-methylhydrazino, 2,2-dimethylhydrazino, 2-ethylhydrazino, hydrazine, 2,2-diethylhydrazino, or the like.

As used herein unless otherwise specified, alkylamino such as "$C_{1-6}$alkylamino" may be mono or dialkylamino such as methylamino, dimethylamino, N-methylethylamino or the like. Similarly, other amino groups such as acylamino are understood to include a $C_{0-6}$alkyl at the unspecified amino bond site (one being to the acyl, the second forming a connection to the core structure, and the third unspecified).

As used herein unless otherwise specified, "ar$C_{0-6}$alkylamino" may be mono or disubstitutedamino such as anilino, benzylamino, N-methylanilino, N-benzylmethylamino or the like.

As used herein unless otherwise specified, "silyl" includes alkyl and aryl substituted silyl groups such as, for example, triethylsilyl, t-butyldiphenylsilyl, or the like.

As used herein unless otherwise specified, "siloxy" includes alkyl and aryl substituted silyloxy groups such as, for example, triethylsilyloxy, t-butyldiphenylsilyloxy, or the like.

As used herein unless otherwise specified, "sulfonyloxy" includes sulfonyloxy groups substituted with aryl, substituted aryl, or alkyl such as, for example, benzenesulfonyl, tosyl, mesyl or the like.

As used herein unless otherwise specified, "heterocyclylamino" includes unsaturated, mono or polycyclic heterocyclic groups containing at least one N-ring atom which is attached to an amino group such as, for example, 1-aminopiperidine, 1-aminomorpholine, 1-amino-4-methylpiperazine or the like.

As used herein unless otherwise specified (for example, by a dash marking the point of attachment), chemical group names comprised of multiple chemical terms are used according to standard chemical convention, wherein each term modifies the following term and wherein the rightmost term forms a covalent bond with the structure to which the substituent is attached. For example, aralkylamino includes benzylamino and phenethylamino attached through the amino nitrogen, but not toluidino or N-methylanilino groups.

Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers. In the present invention, the cyano group pendent on the upper right shown in Formula (I) can be in the cis or trans configuration. The present invention includes both the cis and trans isomers.

The invention also encompasses a pharmaceutical composition that is comprised of a compound of Formula (I) in combination with a pharmaceutically acceptable carrier.

Preferably, the composition is comprised of a pharmaceutically acceptable carrier and a non-toxic therapeutically effective amount of a compound of Formula (I) as described above (or a pharmaceutically acceptable salt or N-oxide thereof).

Moreover, within this preferred embodiment, the invention encompasses a pharmaceutical composition for the treatment of disease by the inhibition of the c-Kit kinase, which may be a wild-type or mutant form of the protein, comprising a pharmaceutically acceptable carrier and a non-toxic therapeutically effective amount of compound of Formula (I) as described above (or a pharmaceutically acceptable salt or N-oxide thereof).

The compounds and compositions of the present invention are effective for treating mammals such as, for example, humans.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, methanesulfonic, and tartaric acids.

The pharmaceutical compositions of the present invention or used by the methods of the present invention comprise a compound represented by Formula (I) (or a pharmaceutically acceptable salt or N-oxide thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula (I), or pharmaceutically acceptable salts or N-oxides thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula (I), or a pharmaceutically acceptable salt or N-oxide thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt or N-oxide of Formula (I). The compounds of Formula (I), or pharmaceutically acceptable salts or N-oxides thereof, can also be included in pharmaceutical compositions in combination with one or more other therapeutically active compounds.

The pharmaceutical compositions of this invention include a pharmaceutically acceptable liposomal formulation containing a compound of Formula (I) or a pharmaceutically acceptable salt or N-oxide thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula (I) of this invention, or a pharmaceutically acceptable salt or N-oxide thereof, via conventional processing methods. As an example, a cream or ointment is prepared by admixing hydrophilic material and water, together with about 5wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula (I), or pharmaceutically acceptable salts or N-oxides thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 10 g per patient per day. For example, breast cancer, head and neck cancers, and gastrointestinal cancer such as colon, rectal or stomach cancer may be effectively treated by the administration of from about 0.01 to 100 mg of the compound per kilogram of body weight per day, or alternatively about 0.5 mg to about 7 g per patient per day.

Similarly, leukemia, ovarian, bronchial, lung, and pancreatic cancer may be effectively treated by the administration of from about 0.01 to 100 mg of the compound per kilogram of body weight per day, or alternatively about 0.5 mg to about 7 g per patient per day.

Mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma may be effectively treated by the administration of from about 0.01 to 100 mg of the compound per kilogram of body weight per day, or alternatively about 0.5 mg to about 7 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention, or pharmaceutically acceptable salts or N-oxides thereof, can also be effectively administered in conjunction with other cancer therapeutic compounds. For example, cytotoxic agents and angiogenesis inhibiting agents can be advantageous co-agents with the compounds of the present invention. Accordingly, the present invention includes compositions comprising the compounds represented by Formula (I), or a pharmaceutically acceptable salt or N-oxide thereof, and a cytotoxic agent or an angiogenesis-inhibiting agent. The amounts of each can be therapeutically effective alone—in which case the additive effects can overcome cancers resistant to treatment by monotherapy. The amounts of any can also be subtherapeutic—to rhinimize adverse effects, particularly in sensitive patients.

It is understood that the treatment of cancer depends on the type of cancer. For example, lung cancer is treated differently as a first line therapy than are colon cancer or breast cancer treated. Even within lung cancer, for example, first line therapy is different from second line therapy, which in turn is different from third line therapy. Newly diagnosed patients might be treated with cisplatinum containing regimens. Were that to fail, they move onto a second line therapy such as a taxane. Finally, if that failed, they might get a tyrosine kinase EGFR inhibitor as a third line therapy. Further, The regulatory approval process differs from country to country. Accordingly, the accepted treatment regimens can differ from country to country. Nevertheless, the compounds of the present invention, or pharmaceutically acceptable salts or N-oxides thereof, can be beneficially co-administered in conjunction or combination with other such cancer therapeutic compounds. Such other compounds include, for example, a variety of cytotoxic agents (alkylators, DNA topoisomerase inhibitors, antimetabolites, tubulin binders); inhibitors of angiogenesis; and different other forms of therapies including kinase inhibitors such as Tarceva, monoclonal antibodies, and cancer vaccines. Other such compounds that can be beneficially co-administered with the compounds of the present invention include doxorubicin, vincristine, cisplatin, carboplatin, gemcitabine, and the taxanes. Thus, the compositions of the present invention include a compound according to Formula (I), or a pharmaceutically acceptable salt or N-oxide thereof, and an anti-neoplastic, anti-tumor, anti-angiogenic, or chemotherapeutic agent.

The compounds of the present invention, or pharmaceutically acceptable salts or N-oxides thereof, can also be effectively administered in conjunction with other therapeutic compounds, aside from cancer therapy. For example, therapeutic agents effective to ameliorate adverse side-effects can be advantageous co-agents with the compounds of the present invention.

C-KIT H526 Cell Assay Protocol

I. Assay for Inhibition of c-Kit in Intact Cells

The ability of compounds to inhibit the tyrosine kinase activity of c-Kit was determined in a cell-based ELISA assay using the H526 cell line (ATCC #CRL-5811), which was originally derived from a human small cell lung cancer. The assay determines the ability of compounds to block ligand-stimulated tyrosine phosphorylation of the wild-type c-Kit receptor protein that is endogenously expressed in H526 cells. Cells are pre-incubated with compounds at various concentrations prior to addition of stem cell factor (SCF), the ligand for the c-Kit receptor tyrosine kinase. Cell lysates are then prepared and the c-Kit protein is captured onto a c-Kit antibody-coated 96-well ELISA plate. The phosphotyrosine content of the receptor protein is then monitored by quantitation of the degree of binding of an antibody that recognizes only the phosphorylated tyrosine residues within the captured protein. The antibody used has a reporter enzyme (e.g. horseradish peroxidase, HRP) covalently attached, such that binding of antibody to phosphorylated c-Kit can be determined quantitatively by incubation with an appropriate HRP substrate.

In the assays below, the following abbreviations are used: HRP for horseradish peroxidase, BSA for bovine serum albumin, EDTA for ehtylenedianinetetraacetic acid, PBS for phosphate-buffered saline, SCF for stem cell factor, DMSO for dimethylsulfoxide, rt for room temperature, min for minute, and h for hour.

The stock reagents used are as follows:

Cell lysis buffer:

50 mM Tris-HCl, pH 7.4

150 mM NaCl

10% Glycerol

1% Triton X-100

0.5 mM EDTA

1 µg/mL leupeptin

1 µg/mL aprotinin 1 mM sodium orthovanadate

Anti c-Kit antibody:

0.5 µg/mL anti c-Kit Ab-3 (Lab Vision, catalog #MS289P1) in 50 mM Sodium bicarbonate, pH 9.

ELISA Assay Plates:

ELISA assay plates are prepared by addition of 100 µL of anti c-Kit antibody to each well of a 96-well Microlite-2 plate (Dynex, catalog #7417), followed by incubation at 37° C. for 2 h. The wells are then washed twice with 300 µL wash buffer.

Plate Wash Buffer:

PBS containing 0.5% Tween-20 (PBST)

Cell Assay Medium:

RPMI with 0.1% BSA pY20-HRP:

25 ng/mL pY20-HRP (Calbiochem, catalog #525320) in PBS, containing 0.5% Tween-20, 5% BSA, 1 mM Sodium orthovanadate HRP Substrate:

Chemoluminescent detection reagent (Pierce, catalog #37075)

Assay Protocol

Cultures of H526 cells, growing in RPMI with 10% fetal calf serum, were collected by centrifugation, washed twice with PBS, and suspended in cell assay medium. Cells were then distributed into a V-bottom 96-well plate at $7.5 \times 10^4$ cells per well in 100 µL cell assay medium.

Compound dilutions were prepared from 10 mM DMSO stocks by dilution in cell assay medium, the final concentration of DMSO in the assay being 0.1%. To compound incubation wells, 50 µL of the test compound was added (compounds are assayed at concentrations between 0.1 nM and 100 µM); to positive and negative control wells, 50 µL cell assay medium containing 0.1% DMSO was added. The cells were then incubated with compound at 37° C. for 3 h. SCF (R&D Systems, catalog #255-SC-010) was then added in order to stimulate the c-Kit receptor and induce its tyrosine phosphorylation. Then, 10 µL of a 1.6 µg/mL solution of SCF in cell assay medium was added to all wells apart from the negative control wells, and the cells were incubated for an additional 15 min at 37° C. Following the addition of ice-cold PBS, the plate was centrifuged at 1000 rpm for 5 min, the medium removed by aspiration, and the cell pellet lysed by the addition of 120 µL ice-cold cell lysis buffer per well. The plate was kept on ice for 20 min and 100 µL of the cell lysates from each well were then transferred to the wells of an ELISA assay plate and incubated at 4° C. for 16 h.

Following incubation of the cell lysates in the ELISA plate, the wells were washed 4 times with 300 µL wash buffer, then 100 µL of the phosphotyrosine detection antibody pY20-HRP was added to each well and the plate incubated at rt for 2 h. The wells were then washed 4 times with 300 µL wash buffer. Then, 50 µL of the chemiluminescent HRP substrate was added to each well for luminometric quantitation of the amount of antiphosphotyrosine-HRP conjugate bound to the plate.

Comparison of the assay signals obtained in the presence of compound with those of the positive and negative controls (cells incubated in the presence or absence of SCF, with no compound added), allows the degree of inhibition of c-Kit receptor tyrosine phosphorylation to be determined over a range of compound concentrations. These inhibition values were fitted to a sigmoidal dose-response inhibition curve to determine the IC50 values (i.e. the concentration of compound that inhibits SCF-induced tyrosine phosphorylation of the c-Kit protein by 50%).

The compounds of this invention reduced the ability of Kit to phosphorylate poly(Glu:Tyr) in the above assay, thus demonstrating direct inhibition of the c-Kit receptor tyrosine kinase activity. $IC_{50}$ values in this assay for the examples described below were between 10 nM and 2.5 µM. $IC_{50}$ values in this assay for COMPOUNDS 1-3 were greater than 50 µM.

Experimental

The EXAMPLES of the present invention were prepared according to the following procedures:

Referring to the scheme shown below, reaction of aminothiophene 1 with aldehydes under reducing conditions affords secondary amines such as compound 2—for example, in the presence of a mixture of triethylsilane and trifluoroacetic acid, or other reagents such as (but not limited to) sodium cyanoborohydride, sodium triacetoxyborohydride, sodium borohydride and hydrogen.

Reaction of the resulting ester with a phenylenediamine under Weinreb amidation conditions (for example, in the presence of alkyl aluminum reagents such as (but not limited to) trimethylaluminum or chlorodimethylaluminum in a neutral solvent such as toluene or dichloromethane (*Synthetic Communications*, (1982), 12, 989)) followed by diphenyl cyanocarbonimidate in 2,2,2-trifluoroethanol gives a mixture of cyanoimidocarbamates such as EXAMPLE 1 or EXAMPLE 2.

Heating these cyanoimidocarbamates in the presence of an amine then yields cyanoguanidines such as EXAMPLE 3.

In the section below, the following abbreviations are used: Me for methyl, Et for ethyl, Ph for phenyl, EtOAc for ethyl acetate, DMSO for dimethylsulfoxide, DCM for dichloromethane, TFA for trifluoroacetic acid, MS for mass spectroscopy, ES for electrospray, rt for room temperature, min for minute, and h for hour.

EXAMPLE 1

Phenyl N'-cyano-N-{3-[({3-[(quinolin-4-ylmethyl)amino]thien-2-yl}carbonyl)amino]phenyl}-imidocarbamate

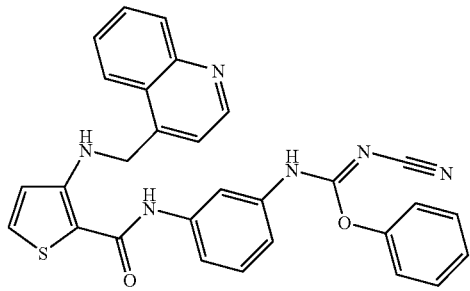

EXAMPLE 2

2,2,2-Trifluoroethyl N'-cyano-N-{3-[({3-[(quinolin-4-ylmethyl)amino]thien-2-yl}carbonyl)amino]phenyl}-imidocarbamate

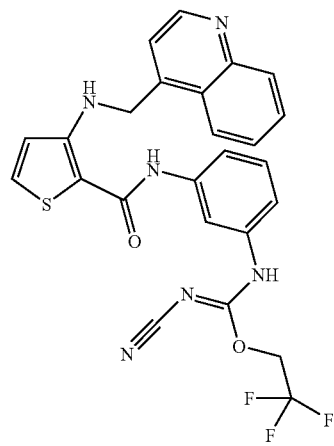

EXAMPLE 1 and EXAMPLE 2 were prepared by the following procedure:

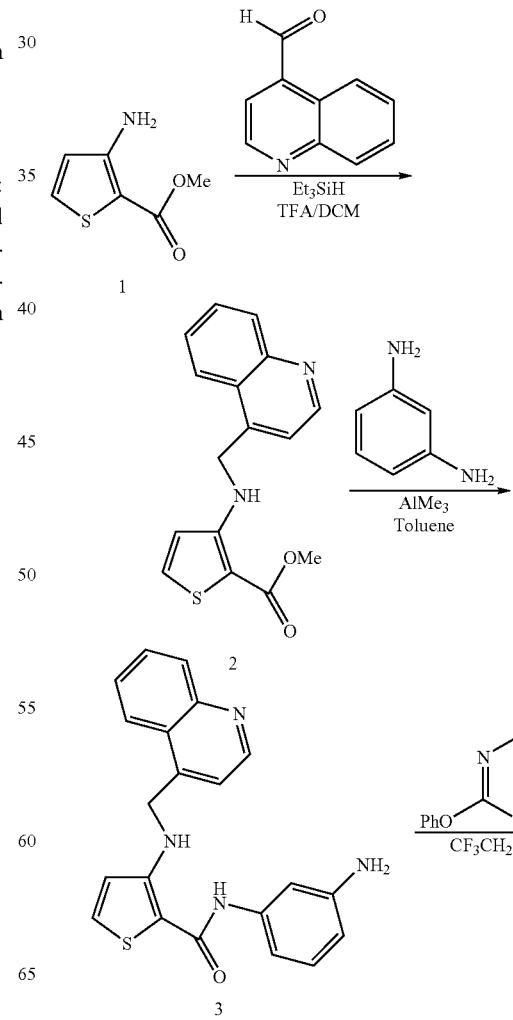

-continued

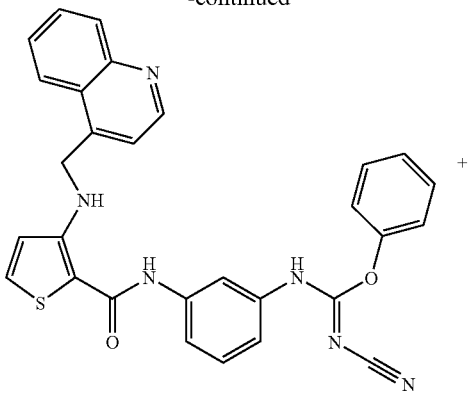

EXAMPLE 1

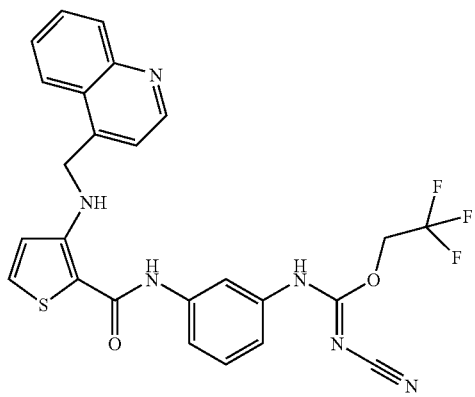

EXAMPLE 2

Part 1:

Methyl 3-[(quinolin-4-ylmethyl)amino]thiophene-2-carboxylate (2): A mixture of 3-amino-thiophene-2-carboxylic acid methyl ester (5 g, 31.8 mmol) and 4-quinoline-carboxaldehyde (5.25 g, 33.4 mmol) in TFA/CH$_2$Cl$_2$ (75 mL, 75 mL) was heated at 50° C. for 3.5 h. The solution was cooled in an ice bath and triethylsilane (10.2 mL, 63.6 mmol) was added drop-wise over 5 min. The reaction mixture was stirred at 50° C. for 3.5 h, cooled to rt, and 500 mL of CH$_2$Cl$_2$ was added. The reaction mixture was basified with 10N NaOH (pH 6-7) followed by sat. NaHCO$_3$ (pH 8). The CH$_2$Cl$_2$ layer was separated and the aqueous layer was extracted with CH$_2$Cl$_2$ (2×10 mL). The organic extracts were combined, washed with brine, dried over anhydrous sodium sulfate, filtered, and concentrated in vacuo to yield the crude product, which was triturated with hexane to give pure methyl 3-[(quinolin-4-ylmethyl)amino]thiophene-2-carboxylate as white solid. MS (ES): m/z 298.55 (100) [MH$^+$]; $^1$H-NMR (400 MHz/CDCl$_3$): δ 3.87 (s, 3H), 5.00 (d, J=4.0 Hz, 2H), 6.48 (d, J=5.6 Hz, 1H), 7.30 (d, J=5.6 Hz, 1H), 7.36 (m, 1H), 7.41 (d, J=4.4 Hz, 1H), 7.62 (t, J=8.0 Hz, 1H), 7.76 (t, J=9.6 Hz, 1H), 8.01 (d, J=8.0 Hz, 1H), 8.17 (d, J=8.4 Hz, 1H), 8.86 (d, J=4.4 Hz, 1H).

Part 2:

N-(3-Aminophenyl)-3-[(quinolin-4-ylmethyl)amino]thiophene-2-carboxamide (3): To a solution of 1,3 phenylenediamine (5.43 g, 50.3 mmol) in anhydrous toluene (100 mL) was added AlMe$_3$ (2M in toluene, 7.5 mL, 15.1 mmol) and the solution was stirred at rt overnight. Methyl 3-[(quinolin-4-ylmethyl)amino]thiophene-2-carboxylate (3 g, 10.05 mmol) was added and the mixture was stirred at 130° C. for 3 h. The reaction mixture was cooled to rt and the toluene was decanted. To the remaining residue, 50 mL of 2N NaOH and 100 mL of CH$_2$Cl$_2$ were added and the solution stirred for 30 min. The CH$_2$Cl$_2$ layer was separated and the aqueous layer was extracted with CH$_2$Cl$_2$ (3×50 mL). The toluene and CH$_2$Cl$_2$ layers were combined, washed with brine, dried over anhydrous sodium sulfate, filtered, and concentrated in vacuo. Purification by silica gel chromatography (50% hexanes:ethyl acetate→100% ethyl acetate) followed by trituration of the solid with CH$_2$Cl$_2$ yielded pure N-(3-aminophenyl)-3-[(quinolin-4-ylmethyl)amino]thiophene-2-carboxamide as a tan powder. MS (ES): m/z 374.86 (100) [MH$^+$]; $^1$H NMR (DMSO-d$^6$, 400 MHz): δ 4.98-4.50 (m, 2H), 5.04 (d, J=5.6 Hz, 2H), 6.25 (d, J=7.2 Hz, 1H), 6.72 (d, J=8.0 Hz, 1H), 6.79 (d, J=5.6 Hz, 1H), 6.89 (t, J=8.0 Hz, 1H), 6.96-6.97 (m, 1H), 7.39 (d, J=4.4 Hz, 1H), 7.55 (d, J=5.6 Hz, 1H), 7.66 (t, J=7.2 Hz, 1H), 7.78 (t, J=6.8 Hz, 1H), 8.00-8.05 (m, 2H), 8.21 (d, J=8.0 Hz, 1H), 8.82 (d, J=4.4 Hz, 1H), 9.08 (s, 1H).

Part 3:

Phenyl N'-cyano-N-{3-[({3-[(quinolin-4-ylmethyl)amino]thien-2-yl}carbonyl)amino]phenyl}imidocarbamate and 2,2,2-trifluoroethyl N'-cyano-N-{3-[({3-[(quinolin-4-ylmethyl)amino]thien-2-yl}carbonyl)amino] phenyl}imidocarbamate: A mixture of N-(3-aminophenyl)-3-[(quinolin-4-ylmethyl)amino]thiophene-2-carboxamide (0.68 g, 1.81 mmol) and diphenyl cyanocarbonimidate (0.45 g, 1.90 mmol) were dissolved in 2,2,2-trifluoroethanol (30 mL) and stirred at rt for 60 h after which a white precipitate formed which was isolated by filtration and washed with ether to yield EXAMPLE 1. MS (ES): m/z 519.2 [M+1]. $^1$H NMR (DMSO-d$^6$, 400 MHz): δ 5.06 (d, J=5.2 Hz, 2H), 6.81 (d, J=5.6 Hz, 1H), 7.14 (d, J=7.6 Hz, 1H), 7.27-7.32 (m, 3H), 7.38-7.45 (m, 3H), 7.50 (d, J=7.6 Hz, 1H), 7.60 (d, J=5.2 Hz, 1H), 7.65 (t, J=7.2 Hz, 1H), 7.78 (t, J=7.2 Hz, 1H), 7.78 (s, 1H), 8.04 (d, J=7.2 Hz, 2H), 8.21 (d, J=8.8 Hz, 1H), 8.80 (d, J=4.8 Hz, 1H), 9.54 (s, 1H), 10.88 (s, 1H). The filtrate was concentrated in vacuo and the resultant gum dissolved in CH$_2$Cl$_2$ and purified by column chromatography (eluting with 1:1 hexanes/EtOAc to 1:4 hexanes/EtOAc) to yield EXAMPLE 2 as a white powder. MS (ES): m/z 524.8 [M+1]. $^1$H NMR (DMSO-$^6$, 400 MHz): δ 4.93 (d, J=8.8 Hz, 2H), 5.06 (s, 2H), 6.81 (d, J=5.6 Hz, 1H), 6.90-6.97 (m, 1H), 7.28 (brs, 1H), 7.39 (d, J=4.0 Hz, 1H), 7.47 (brs, 1H), 7.60 (d, J=3.2 Hz, 1H), 7.65 (t, J=6.8 Hz, 1H), 7.73 (brs, 1H), 7.77 (t, J=6.8 Hz, 1H), 8.04 (d, J=8.4 Hz, 2H), 8.21 (d, J=8.4 Hz, 1H), 8.82 (d, J=4.4 Hz, 1H), 9.50 (s, 1H), 10.83 (s, 1H).

EXAMPLE 3

N-(3-{[amino(cyanoimino)methyl]-amino}phenyl)-3-((quinolin-4-ylmethyl)amino)thiophene-2-carboxamide

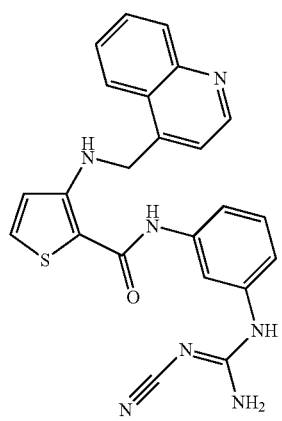

EXAMPLE 3 was prepared by the following procedure:

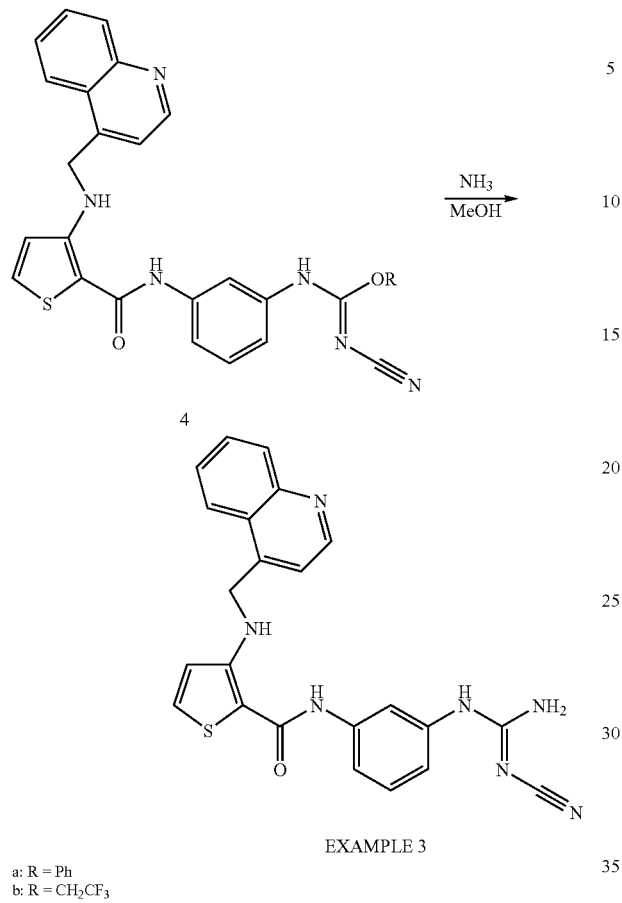

a: R = Ph
b: R = CH2CF3

EXAMPLE 3

To a solution of phenyl N'-cyano-N-{3-[({3-[(quinolin-4-ylmethyl)amino]thien-2-yl}carbonyl)amino]phenyl}imidocarbamate (4a, EXAMPLE 1) or 2,2,2-trifluoroethyl N'-cyano-N-{3-[({3-[(quinolin-4-ylmethyl)amino]thien-2-yl}carbonyl)amino]phenyl}imidocarbamate (4b, EXAMPLE 2) (50 mg) in DMSO (150 μL) was added a solution of ammonia in methanol (650 μL). The reaction was heated to 50° C. for 6 h then left at rt overnight. The reaction was cooled to rt, concentrated, and purified by reverse phase HPLC to provide EXAMPLE 3. MS (ES): m/z 442.1 [M+1]. $^1$H NMR (DMSO-d$^6$, 400 MHz): δ 5.06 (d, J=5.2 Hz, 2H), 6.79 (d, J=5.6 Hz, 1H), 6.96 (s, 1H), 7.03 (d, J=8.4 Hz, 1H), 7.20 (t, J=8.0 Hz, 1H), 7.36 (d, J=8.4 Hz, 1H), 7.39 (d, J=4.0 Hz, 1H), 7.58 (d, J=5.2 Hz, 1H), 7.66 (t, J=7.2 Hz, 1H), 7.75 (s, 1H), 7.79 (t, J=7.2 Hz, 1H), 8.01-8.05 (m, 2H), 8.21 (d, J=8.8 Hz, 1H), 8.82 (d, J=4.4 Hz, 1H), 9.06 (s, 1H), 9.44 (s, 1H).

The following analogues were prepared using phenyl N'-cyano-N-{3-[({3-[(quinolin-4-ylmethyl)amino]thien-2-yl}carbonyl)amino]phenyl}imidocarbamate (EXAMPLE 1) or 2,2,2-Trifluoroethyl N'-Cyano-N-{3-[({3-[(quinolin-4-ylmethyl)amino]thien-2-yl}carbonyl)amino]phenyl}imidocarbamate (EXAMPLE 2) and the appropriate amine, according to the procedure described above for EXAMPLE 3.

EXAMPLE 4
N-(3-{[(Cyanoimino)(methylamino)-methyl]amino}phenyl)-3-((quinolin-4-ylmethyl)amino)thiophene-2-carboxamide: MS (ES) 456.2 [M+1]

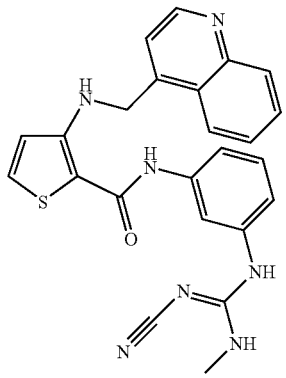

EXAMPLE 5
N-(3-{[(Cyanoimino)(4-methylpiperazin-1-yl)methyl]amino}phenyl)-3-((quinolin-4-ylmethyl)amino)thiophene-2-carboxamide: MS (ES) 525.2 [M+1]

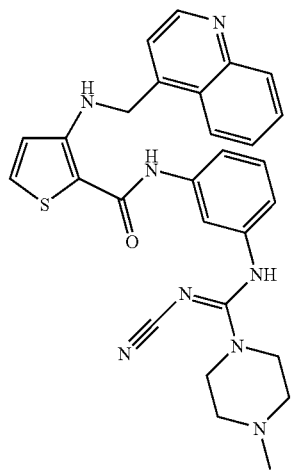

EXAMPLE 6
N-(3-{[(Cyanoimino)(2-methoxyethylamino)methyl]-amino}phenyl)-3-((quinolin-4-ylmethyl)amino)thiophene-2-carboxamide: MS (ES) 499.8 [M+1]

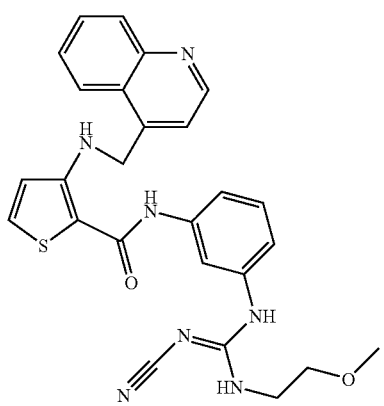

EXAMPLE 7
N-(3-{[(Cyanoimino)(2-(dimethylamino)ethylamino)-methyl]amino}phenyl)-3-((quinolin-4-ylmethyl)amino)thiophene-2-carboxamide: MS (ES) 512.6 [M+1]

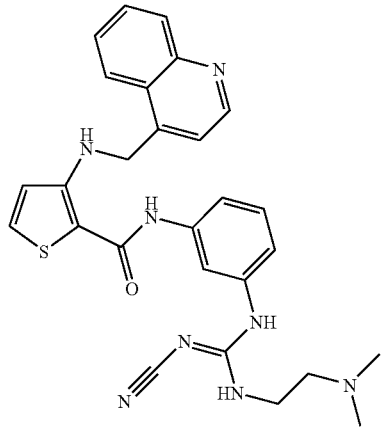

EXAMPLE 8

N-(3-{[(Cyanoimino)(piperazin-1-yl)methyl]amino}phenyl)-3-((quinolin-4-ylmethyl)amino)thiophene-2-carboxamide: MS (ES) 511.3 [M+1]

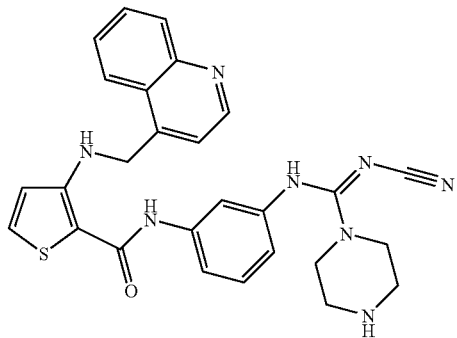

EXAMPLE 9
N-(3-{[(Cyanoimino)(3-hydroxypyirrolidin-1-yl)methyl]amino}phenyl)-3-((quinolin-4-ylmethyl)amino)thiophene-2-carboxamide: MS (ES) 512.0 [M+1]

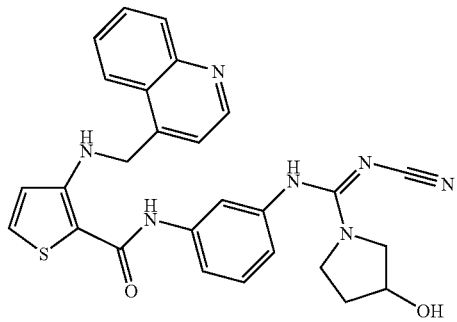

EXAMPLE 10
N-(3-{[(Cyanoimino)(2-morpholine-4-ylethylamino)methyl]amino}phenyl)-3-((quinolin-4-ylmethyl)amino)thiophene-2-carboxamide: MS (ES) 555.0 [M+1]

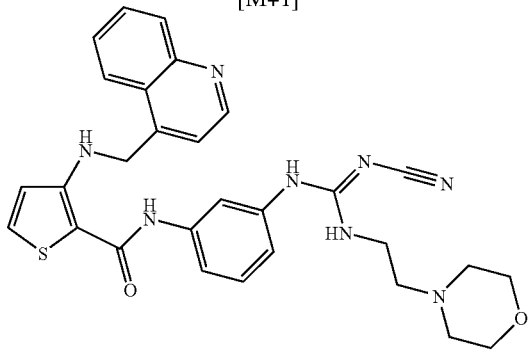

EXAMPLE 11
N-(3-{[(Cyanoimino)(3-(1H-imidazolyl)propylamino)methyl]-amino}phenyl)-3-((quinolin-4-ylmethyl)amino)thiophene-2-carboxamide: MS (ES) 550.3 [M+1]

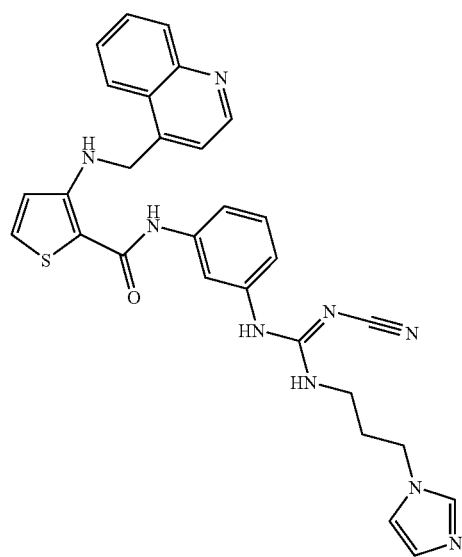

EXAMPLE 12
N-(3-{[(Cyanoimino)(piperidin-1-yl)methyl]amino}phenyl)-3-((quinolin-4-ylmethyl)amino)thiophene-2-carboxamide: MS (ES) 509.8 [M+1]

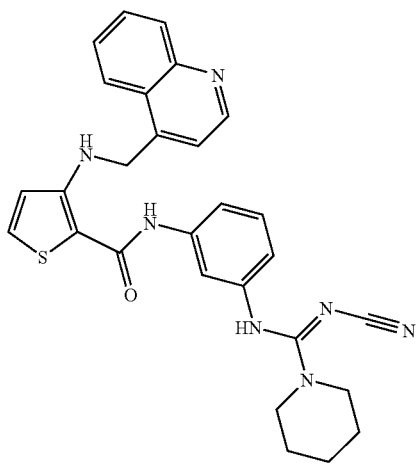

EXAMPLE 13
N-(3-{[(Cyanoimino)(2-piperidine-1-ylethylamino)methyl]amino}-phenyl)-3-((quinolin-4-ylmethyl)amino)thiophene-2-carboxamide: MS (ES) 553.0 [M+1]

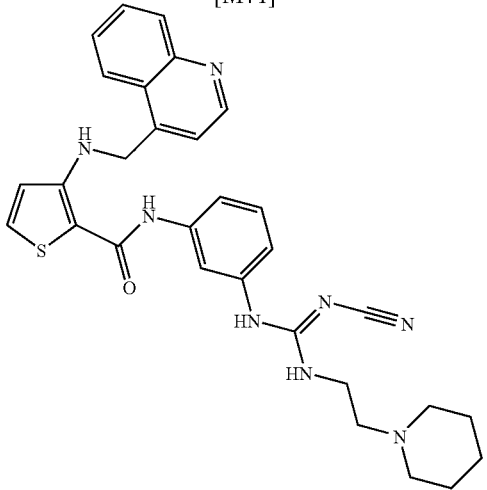

EXAMPLE 14
N-(3-{[(cyanoimino)(dimethylamino)-methyl]amino}phenyl)-3-((quinolin-4-ylmethyl)amino)thiophene-2-carboxamide: MS (ES) 469.9 [M+1]

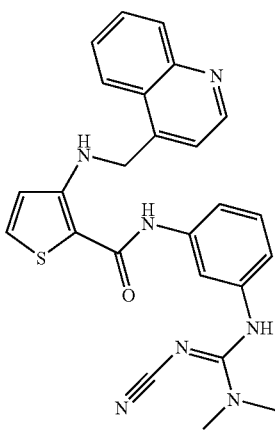

EXAMPLE 15
N-(3-{[(Cyanoimino)(4-hydroxypiperidin-1-yl)methyl]amino}phenyl)-3-((quinolin-4-ylmethyl)amino)thiophene-2-carboxamide: MS (ES) 526.0 [M+1]

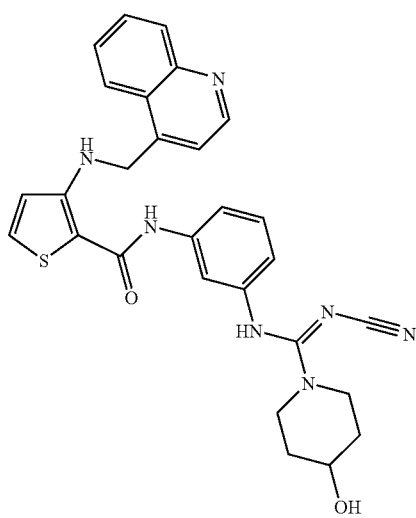

EXAMPLE 16

N-(3-{[(Cyanoimino)(cyclohexylamino)methyl]amino}phenyl)-3-((quinolin-4-ylmethyl)amino)thiophene-2-carboxamide: MS (ES) 523.9 [M+1]

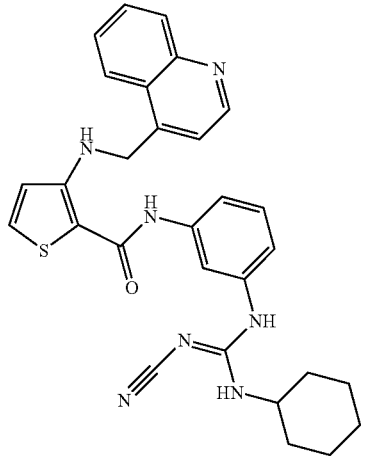

EXAMPLE 17

N-(3-{[(Cyanoimino)(2-(1-methylpyrrolidin-2-yl)ethylamino)methyl]amino}-phenyl)-3-((quinolin-4-ylmethyl)amino)thiophene-2-carboxamide: MS (ES) 553.0 [M+1]

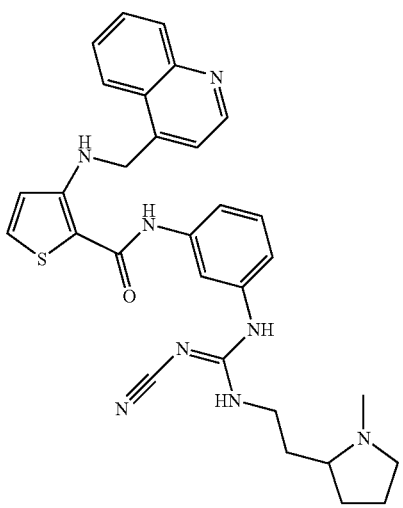

EXAMPLE 18

N-(3-{[(Cyanoimino)(pyridine-3-ylmethylamino)methyl]amino}-phenyl)-3-((quinolin-4-ylmethyl)amino)thiophene-2-carboxamide: MS (ES) 533.2 [M+1]

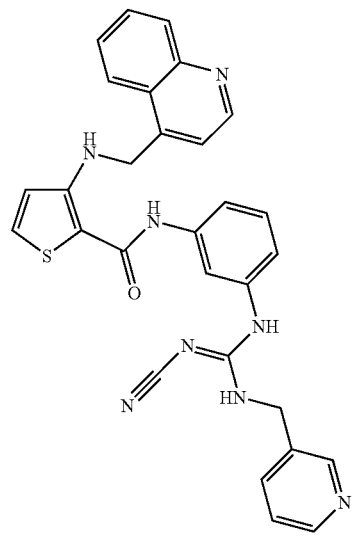

EXAMPLE 20

N-(3-{[(Cyanoimino)(bis(2-methoxyethyl)amino)methyl]-amino}phenyl)-3-((quinolin-4-ylmethyl)amino)thiophene-2-carboxamide: MS (ES) 557.9 [M+1]

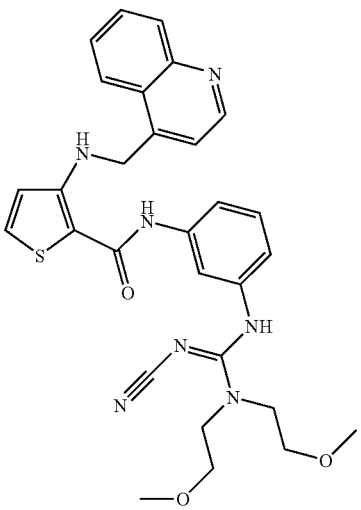

EXAMPLE 19

N-(3-{[(Cyanoimino)(morpholin-4-yl)methyl]amino}phenyl)-3-((quinolin-4-ylmethyl)amino)thiophene-2-carboxamide: MS (ES) 512.1 [M+1]

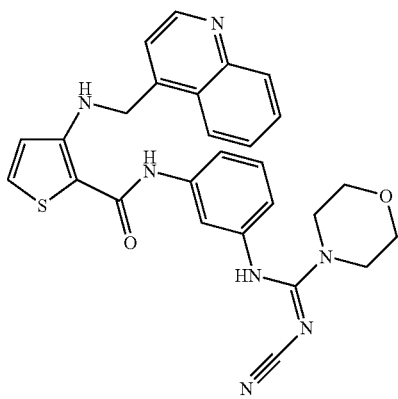

EXAMPLE 21

Phenyl N-[2-chloro-5-({[3-((quinolin-4-ylmethyl)amino)thien-2-yl]carbonyl}amino)phenyl]-N'-cyanoimidocarbamate

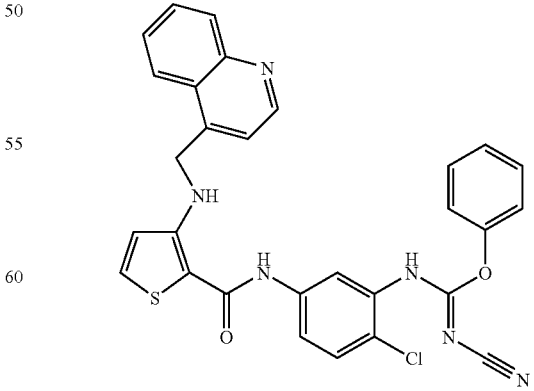

EXAMPLE 21 was prepared according to the procedure described for EXAMPLE 1 using 4-chloro-1,3-phenylenediamine instead of 1,3-phenylene diamine: MS (ES) 553 [M+1], 555 [M+3].

COMPOUND 1

2,2,2-Trifluoroethyl N-{2-chloro-5-[({3-[(quinolin-4-ylmethyl)amino]thien-2-yl}carbonyl)amino]phenyl}-N'-cyanoimidocarbamate

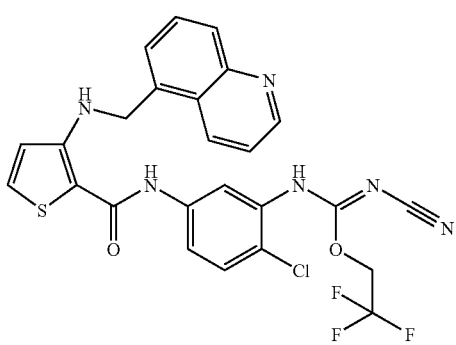

COMPOUND 1 was prepared according to the procedure described for EXAMPLE 2 using 4-chloro-1,3-phenylenediamine instead of 1,3-phenylene diamine: MS (ES) 558.9 [M+1], 560.9 [M+3].

COMPOUND 2

2,2,2-Trifluoroethyl N'-cyano-N-{4-[({3-[(quinolin-4-ylmethyl)amino]thien-2-yl}carbonyl)amino]phenyl)}-imidocarbamate

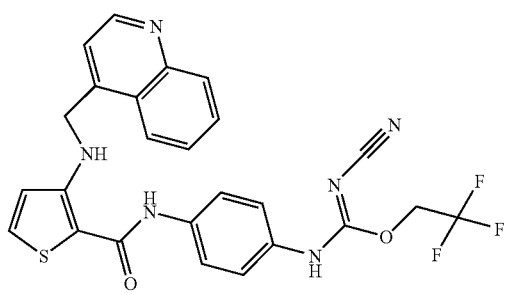

COMPOUND 2 was prepared according to the procedure described for EXAMPLE 2 using 1,4-phenylenediamine instead of 1,3-phenylenediamine: MS (ES) 525 [M+1].

The following analogues were prepared using 2,2,2-trifluoroethyl N'-cyano-N-{4-[({3-[(quinolin-4-ylmethyl)amino]thien-2-yl}carbonyl)amino]phenyl}-imidocarbamate (COMPOUND 2) and the appropriate amine, according to the procedure described above for EXAMPLE 3.

EXAMPLE 22

N-(4-{[(Cyanoimino)(dimethylamino)-methyl]amino}phenyl)-3-((quinolin-4-ylmethyl)amino)thiophene-2-carboxamide: MS (ES) 470 [M+1]

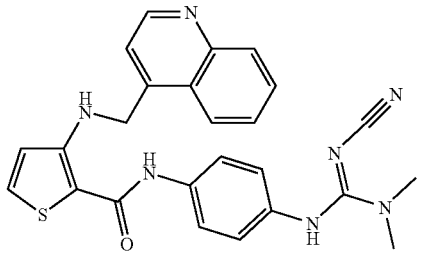

EXAMPLE 23

N-(4-{[(Cyanoimino)(morpholin-4-yl)methyl]amino}phenyl)-3-((quinolin-4-ylmethyl)amino)thiophene-2-carboxamide: MS (ES) 512 [M+1]

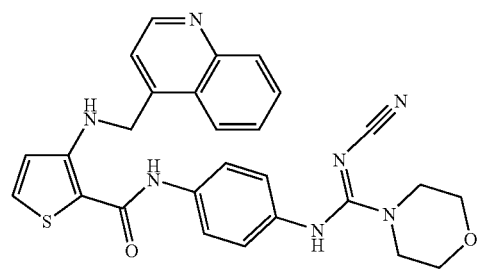

EXAMPLE 24

N-(4-{[Amino(cyanoimino)methyl]-amino}phenyl)-3-((quinolin-4-ylmethyl)amino)thiophene-2-carboxamide: MS (ES) 442 [M+1]

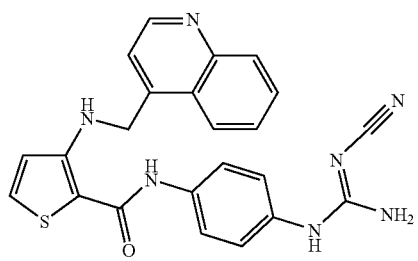

EXAMPLE 25
N-(4-{[(Cyanoimino)(methylamino)-methyl]amino}phenyl)-3-((quinolin-4-ylmethyl)amino)thiophene-2-carboxamide: MS (ES) 456 [M+1]

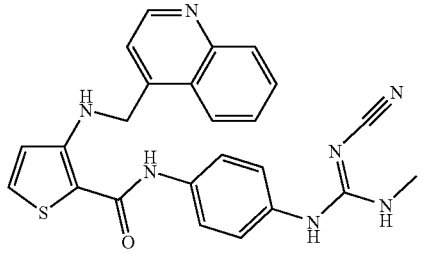

EXAMPLE 26
N-(4-{[(Cyanoimino)(2-methoxyethylamino)methyl]-amino}phenyl)-3-((quinolin-4-ylmethyl)amino)thiophene-2-carboxamide: MS (ES) 500 [M+1]

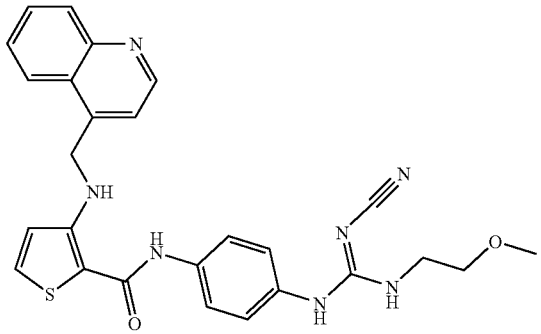

The following analogues were prepared using phenyl N'-cyano-N-{3-chloro-5-[({3-[(quinolin-4-ylmethyl)amino]thien-2-yl}carbonyl)amino]phenyl}imidocarbamate (prepared according to EXAMPLE 1 using 5-chloro-1,3-phenylenediamine instead of 1,3-phenylenediamine) and the appropriate amine, according to the procedure described above for EXAMPLE 3.

EXAMPLE 27
N-(3-{[(Cyanoimino)(methylamino)-methyl]amino}-5-chlorophenyl)-3-((quinolin-4-ylmethyl)amino)thiophene-2-carboxamide: MS (ES) 490 [M+1], 492 [M+3]

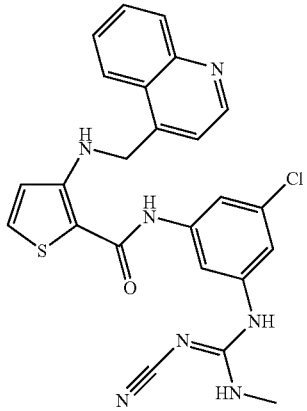

EXAMPLE 28
N-(3-{[Amino(cyanoimino)methyl]-amino}-5-chlorophenyl)-3-((quinolin-4-ylmethyl)amino)thiophene-2-carboxamide: MS (ES) 475 [M+1], 477 [M+3]

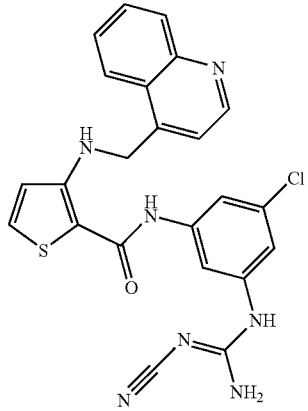

EXAMPLE 29
N-(3-{[(Cyanoimino)(dimethylamino)-methyl]amino}-5-chlorophenyl)-3-((quinolin-4-ylmethyl)amino)thiophene-2-carboxamide: MS (ES) 503 [M+1], 505 [M+3]

EXAMPLE 30
N-(3-{[(Cyanoimino)(2-methoxyethylamino)methyl]-amino}-5-chlorophenyl)-3-((quinolin-4-ylmethyl)amino)thiophene-2-carboxamide: MS (ES) 533 [M+1], 535 [M+3]

EXAMPLE 31

N-(3-{[(Cyanoimino)(2-(dimethylamino)ethylamino)-methyl]amino}-5-chlorophenyl)-3-((quinolin-4-ylmethyl)amino)thiophene-2-carboxamide: MS (ES) 546 [M+1], 548 [M+3]

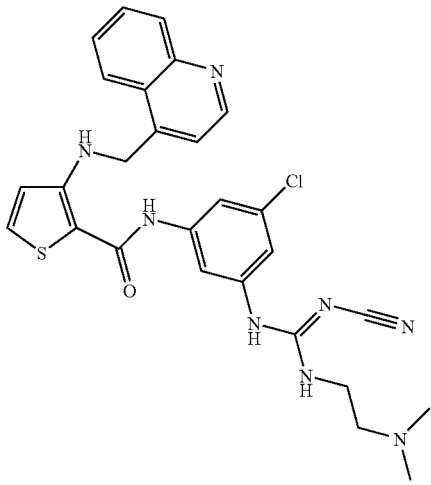

EXAMPLE 32

N-(3-{[(Cyanoimino)(2-morpholine-4-ylethylamino)methyl]amino}-5-chlorophenyl)-3-((quinolin-4-ylmethyl)amino)thiophene-2-carboxamide: MS (ES) 588 [M+1], 590 [M+3]

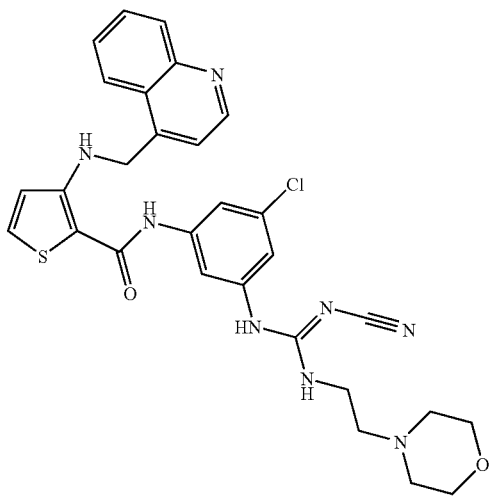

The following analogues were prepared using phenyl N'-cyano-N-{3-trifluoromethyl-5-[({3-[(quinolin-4-ylmethyl)amino]thien-2-yl}carbonyl)amino]phenyl}imidocarbamate (prepared according to EXAMPLE 1 using 5-trifluoro methyl-1,3-phenylenediamine instead of 1,3-phenylenediamine) and the appropriate amine, according to the procedure described above for EXAMPLE 3.

EXAMPLE 33

N-(3-{[Amino(cyanoimino)methyl]-amino}-5-trifluoromethylphenyl)-3-((quinolin-4-ylmethyl)amino)thiophene-2-carboxamide: MS (ES) 510 [M+1]

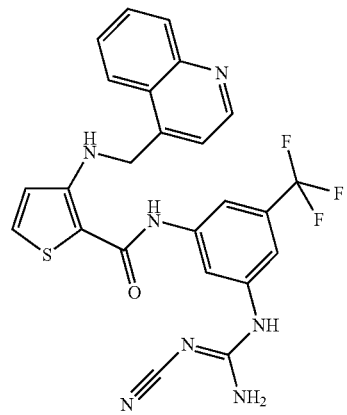

EXAMPLE 34

N-(3-{[(Cyanoimino)(dimethylamino)-methyl]amino}-5-trifluoromethylphenyl)-3-((quinolin-4-ylmethyl)amino)thiophene-2-carboxamide: MS (ES) 538 [M+1]

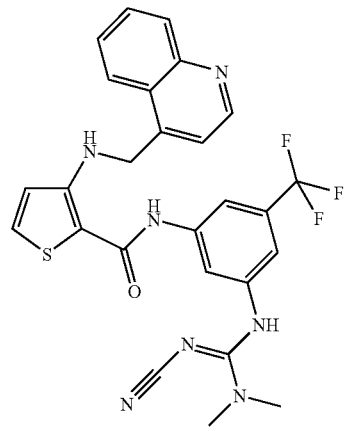

EXAMPLE 35

N-(3-{[(Cyanoimino)(2-methoxyethylamino)methyl]-amino}-5-trifluoromethylphenyl)-3-((quinolin-4-ylmethyl)amino)thiophene-2-carboxamide: MS (ES) 568 [M+1]

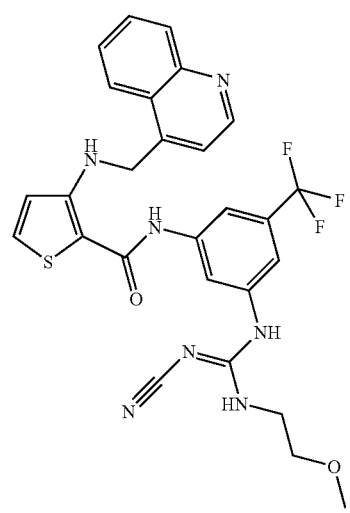

EXAMPLE 36

N-(3-{[(Cyanoimino)(2-(dimethylamino)ethylamino)-methyl]amino}-5-trifluoromethylphenyl)-3-((quinolin-4-ylmethyl)amino)thiophene-2-carboxamide: MS (ES) 581 [M+1]

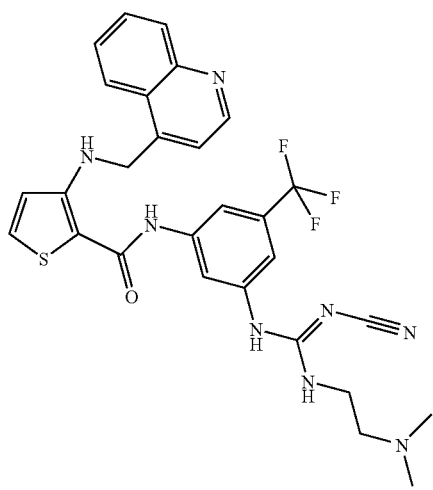

EXAMPLE 37

N-(3-{[(Cyanoimino)(2-morpholine-4-ylethylamino)methyl]amino}-5-trifluoromethylphenyl)-3-((quinolin-4-ylmethyl)amino)thiophene-2-carboxamide: MS (ES) 623 [M+1]

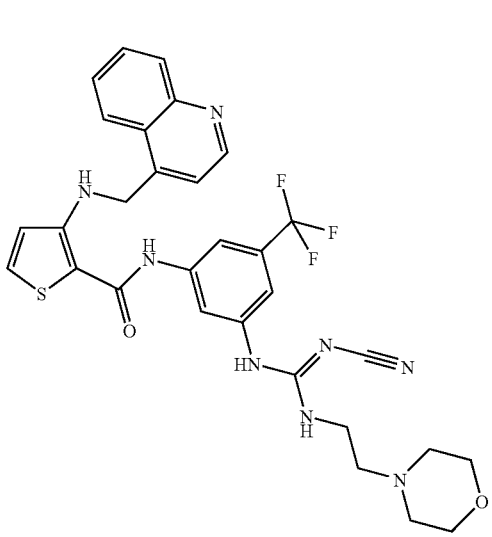

EXAMPLE 38

N-(3-{[(Cyanoimino)(2-morpholine-4-yl)methyl]amino}-5-trifluoromethylphenyl)-3-((quinolin-4-ylmethyl)amino)thiophene-2-carboxamide: MS (ES) 580 [M+1]

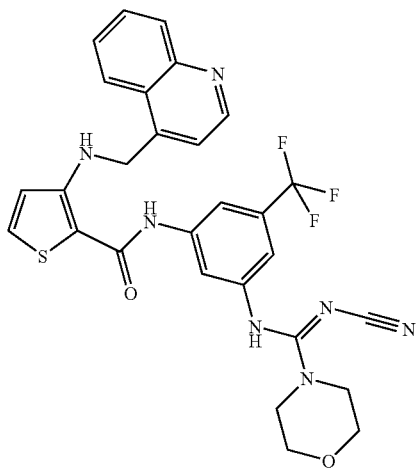

EXAMPLE 39

N-(3-{[(Cyanoimino)(4-methylpiperazin-1-yl)methyl]amino}-5-trifluoromethylphenyl)-3-((quinolin-4-ylmethyl)amino)thiophene-2-carboxamide: MS (ES) 592.9 [M+1]

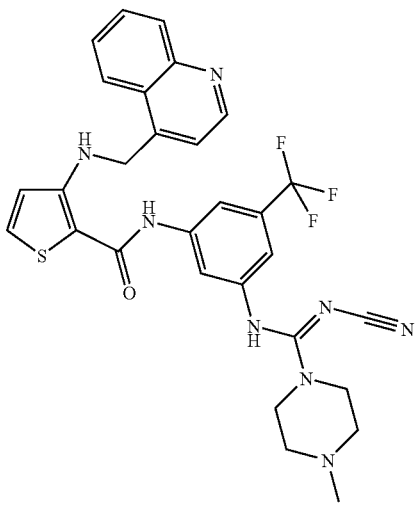

EXAMPLE 40

N-(3-{[(Cyanoimino)(3-hydroxypyrrolidin-1-yl)methyl]amino}-5-trifluoromethylphenyl)-3-((quinolin-4-ylmethyl)amino)thiophene-2-carboxamide: MS (ES) 579.8 [M+1]

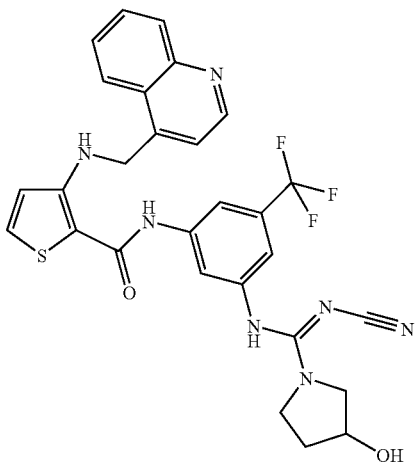

EXAMPLE 41

N-(3-{[(Cyanoimino)(3-(1H-imidazolyl)propylamino)methyl]-amino}-5-trifluoromethylphenyl)-3-((quinolin-4-ylmethyl)amino)thiophene-2-carboxamide: MS (ES) 617.2 [M+1]

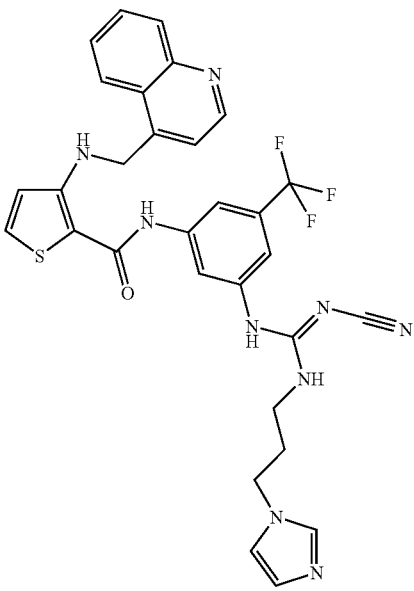

EXAMPLE 42

(2R)-1-[{[3-{[(3-((quinolin-4-ylmethyl)amino)thien-2-yl)carbonyl]amino}-5-(trifluoromethyl)phenyl]amino}-(cyanoimino)methyl]pyrrolidine-2-carboxamide: MS (ES) 606.7 [M+1]

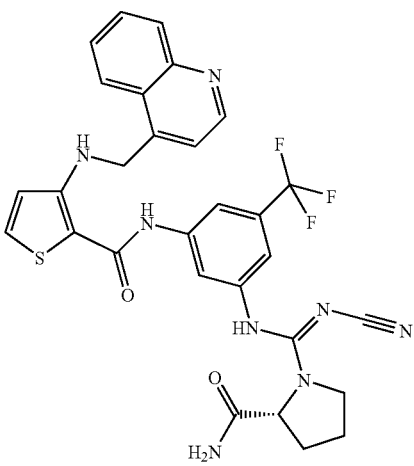

EXAMPLE 43

N-(3-{[(Cyanoimino)(pyridine-3-ylmethylamino)methyl]amino}-5-trifluoromethylphenyl)-3-((quinolin-4-ylmethyl)amino)thiophene-2-carboxamide: MS (ES) 600.6 [M+1]

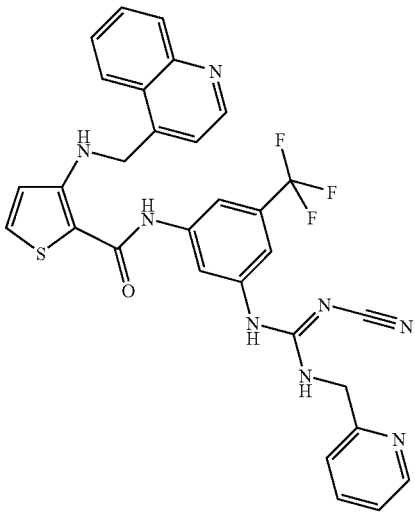

EXAMPLE 44

N-(3-{[(Cyanoimino)(methylamino)-methyl]amino}-5-trifluoromethylphenyl)-3-((quinolin-4-ylmethyl)amino)thiophene-2-carboxamide: MS (ES) 523.5 [M+1]

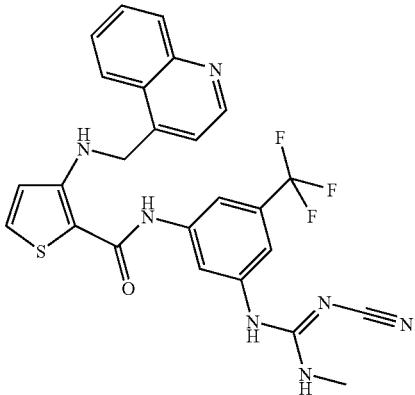

EXAMPLE 45

2,2,2-Trifluoroethyl N'-cyano-N-{2-methyl-5-[({3-[(quinolin-4-ylmethyl)amino]thien-2-yl}carbonyl)amino]phenyl}-imidocarbamate

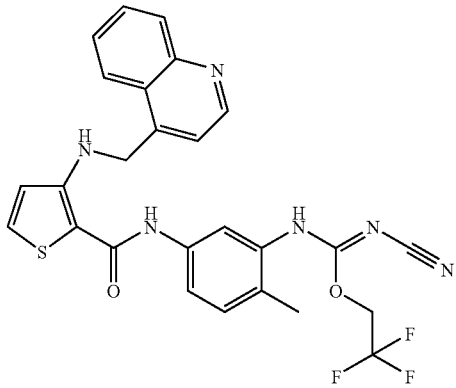

EXAMPLE 45 was prepared according to EXAMPLE 2 using 4-methyl-1,3-phenylenediamine instead of 1,3-phenylenediamine: MS (ES) 539.0 [M+1].

The following analogues were prepared using 2,2,2-trifluoroethyl N'-cyano-N-{2-methyl-5-[({3-[(quinolin-4-ylmethyl)amino]thien-2-yl}carbonyl)amino]phenyl}-imidocarbamate (EXAMPLE 45) and the appropriate amine, according to the procedure described above for EXAMPLE 3.

EXAMPLE 46

N-(3-{[(Cyanoimino)(methylamino)-methyl]amino}-4-methylphenyl)-3-((quinolin-4-ylmethyl)amino)thiophene-2-carboxamide: MS (ES) 470 [M+1]

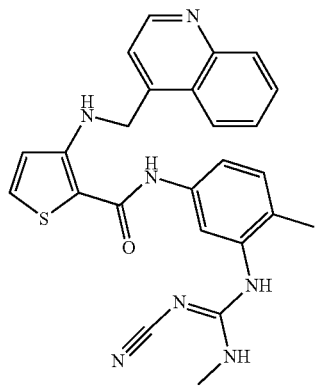

EXAMPLE 47

N-(3-{[(Cyanoimino)(dimethylamino)-methyl]amino}-4-methylphenyl)-3-((quinolin-4-ylmethyl)amino)thiophene-2-carboxamide: MS (ES) 483.9 [M+1]

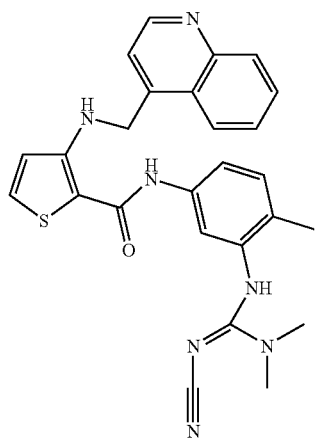

EXAMPLE 48

N-(3-{[(Cyanoimino)(2-methoxyethylamino)methyl]-amino}-4-methylphenyl)-3-((quinolin-4-ylmethyl)amino)thiophene-2-carboxamide: MS (ES) 513.9 [M+1]

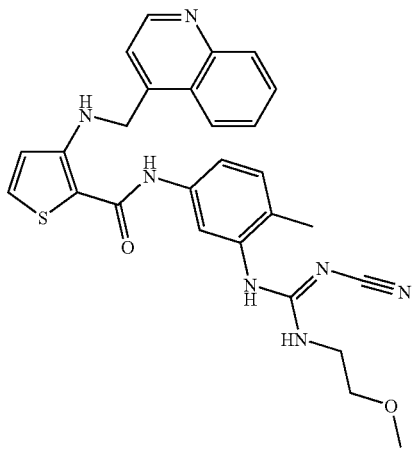

The following analogues were prepared using phenyl N'-cyano-N-{3-[({3-[(quinolin-4-ylmethyl)amino]thien-2-yl}carbonyl)amino]phenyl}imidocarbamate (EXAMPLE 1) or 2,2,2-trifluoroethyl N'-Cyano-N-{3-[({3-[(quinolin-4-ylmethyl)amino]thien-2-yl}carbonyl)amino]phenyl}imidocarbamate (EXAMPLE 2) and the appropriate amine, according to the procedure described for EXAMPLE 3.

EXAMPLE 49

(2R)-1-[{[3-{[(3-((quinolin-4-ylmethyl)amino)thien-2-yl)carbonyl]amino}phenyl]amino}(cyanoimino)methyl]pyrrolidine-2-carboxamide: MS (ES) 539 [M+1]

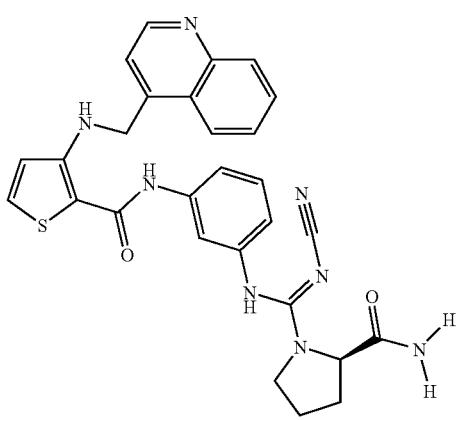

EXAMPLE 50

(2S)-1-[{[3-{[(3-((quinolin-4-ylmethyl)amino)thien-2-yl)carbonyl]amino}phenyl]amino}(cyanoimino)methyl]pyrrolidine-2-carboxamide: MS (ES) 539 [M+1]

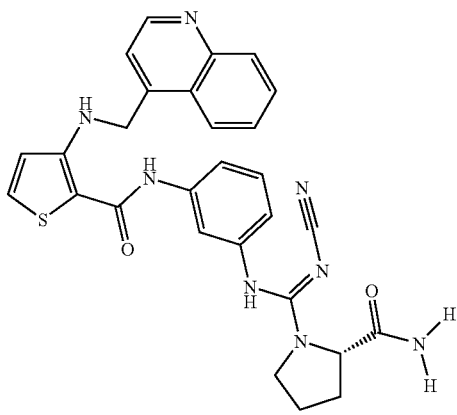

EXAMPLE 51

Phenyl N-cyano-6-({[3-((quinolin-4-ylmethyl)amino)thien-2-yl]carbonyl}amino)indoline-1-carboximidoate

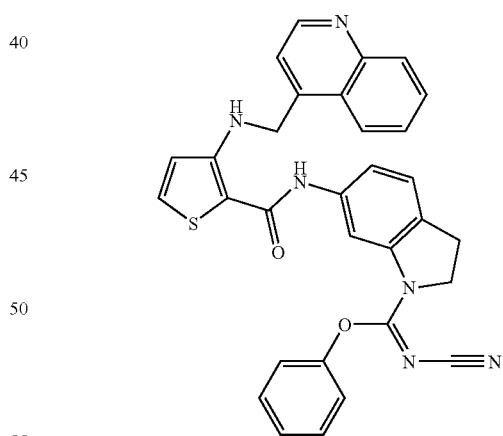

EXAMPLE 51 was prepared according to EXAMPLE 1 using 6-aminoindoline instead of 1,3-phenylenediamine: MS (ES) 545 [M+1].

The following analogues were prepared using phenyl N-cyano-6-({[3-((quinolin-4-ylmethyl)amino)thien-2-yl]carbonyl}amino)indoline-1-carboximidoate (EXAMPLE 51) and the appropriate amine, according to the procedure described above for EXAMPLE 3.

EXAMPLE 52
N-{1-[(Cyanoimino)(methylamino)methyl]-2,3-dihydro-1H-indol-6-yl}-3-((quinolin-4-ylmethyl)amino)thiophene-2-carboxamide: MS (ES) 482 [M+1]

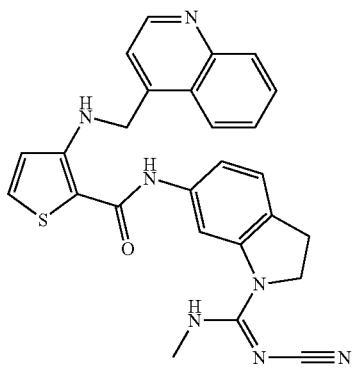

EXAMPLE 53
N-{1-[(Cyanoimino)(2-methoxyethylamino)methyl]-2,3-dihydro-1H-indol-6-yl}-3-((quinolin-4-ylmethyl)amino)thiophene-2-carboxamide: MS (ES) 526 [M+1]

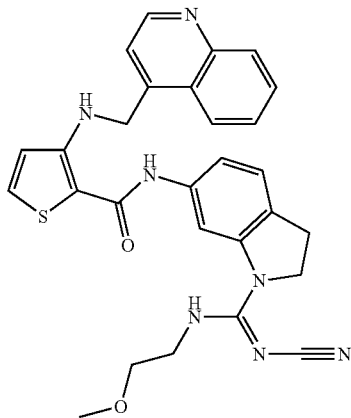

EXAMPLE 54
N-{1-[(Cyanoimino)(4-methylpiperazin-1-yl)methyl]-2,3-dihydro-1H-indol-6-yl}-3-((quinolin-4-ylmethyl)amino)thiophene-2-carboxamide: MS (ES) 551 [M+1]

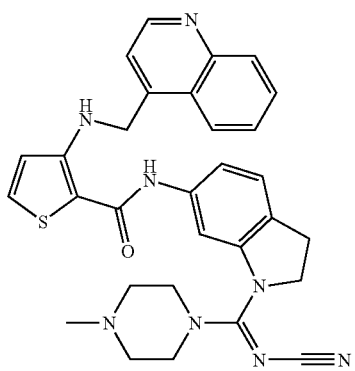

EXAMPLE 55
N-{1-[(Cyanoimino)(pyrrolidin-1-yl)methyl]-2,3-dihydro-1H-indol-6-yl}-3-((quinolin-4-ylmethyl)amino)thiophene-2-carboxamide: MS (ES) 522 [M+1]

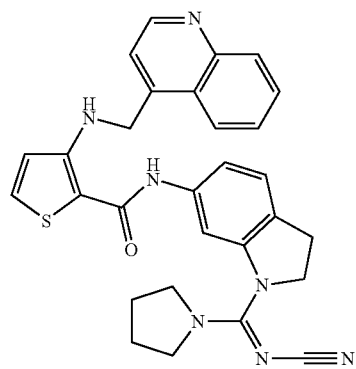

EXAMPLE 56
N-{1-[amino(cyanoimino)methyl]-2,3-dihydro-1H-indol-6-yl}-3-[(quinolin-4-ylmethyl)amino]thiophene-2-carboxamide: MS (ES) 468 [M+1]

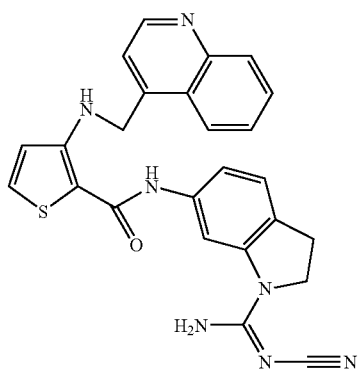

EXAMPLE 57
N-{1-[(Cyanoimino)(2-morpholine-4-yl)methyl]-2,3-dihydro-1H-indol-6-yl}-3-((quinolin-4-ylmethyl)amino)thiophene-2-carboxamide: MS (ES) 538 [M+1]

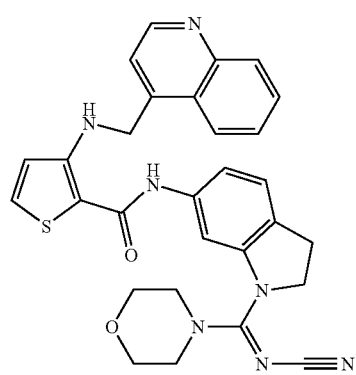

COMPOUND 3

N-{1-[(Cyanoimino)(dimethylamino)methyl]-2,3-dihydro-1H-indol-6-yl}-3-((quinolin-4-ylmethyl)amino)thiophene-2-carboxamide: MS (ES) 496 [M+1]

What is claimed is:

1. A compound of Formula (I):

(I)

wherein:

Q is thienyl optionally substituted with 1-2 independent $R^3$ substituents;

Y is aryl which is optionally substituted with 1-4 independent $R^{31}$ substituents;

J is —$NR^1R^2$, —$OR^1$, or —$SR^1$;

A is quinolinyl which is optionally substituted by 1-5 independent $R^4$ substituents;

$R^1$ and $R^2$ are $C_{0-6}$alkyl, aryl, cyclo$C_{3-10}$alkyl, cyclo$C_{3-10}$alkenyl, $C_{2-6}$alkenyl, $C_{2-6}$alkynyl, each of which is optionally substituted by 1-5 independent $R^{41}$ substituents;

$R^3$ and $R^{31}$ each independently is $C_{0-6}$alkyl, cyclo$C_{3-10}$alkyl, haloalkyl, halogen, cyano$C_{0-6}$alkyl, nitro$C_{0-6}$alkyl, hydroxy$C_{0-6}$alkyl, $C_{0-6}$alkylamino$C_{0-6}$alkyl, acyl$C_{0-6}$alkyl, substituted acyl, acylamino$C_{0-6}$alkyl, substituted acylamino, acyloxy$C_{0-6}$alkyl, substituted acyloxy, ar$C_{0-6}$alkyl, heteroaryl$C_{0-6}$alkyl, arylhydrazino, alkylsulfonamido$C_{0-6}$alkyl, arylsulfonamido$C_{0-6}$alkyl, alkylsulfonyl$C_{0-6}$alkyl, arylsulfonyl$C_{0-6}$alkyl, alkylsulfinyl$C_{0-6}$alkyl, heterocyclylsulfonyl$C_{0-6}$alkyl, silyl, siloxy$C_{0-6}$alkyl, alkenoxy$C_{0-6}$alkyl, alkynoxy$C_{0-6}$alkyl, $C_{0-6}$alkoxy$C_{0-6}$alkyl, $C_{1-6}$alkylthio$C_{0-6}$alkyl, $C_{2-6}$alkenyl, acyl$C_{2-6}$alkenyl, $C_{2-6}$alkynyl, acyl$C_{2-6}$alkynyl, ar$C_{0-6}$alkylamino$C_{0-6}$alkyl, ar$C_{0-6}$alkylthio$C_{0-6}$alkyl, ar$C_{0-6}$alkoxy$C_{0-6}$alkyl, substituted ar$C_{0-6}$alkoxy, substituted ar$C_{0-6}$alkylthio, or substituted ar$C_{0-6}$alkoxy;

$R^4$ and $R^{41}$ each independently is $C_{0-6}$alkyl, cyclo$C_{3-10}$alkyl, oxo, halogen, haloalkyl, cyano$C_{0-6}$alkyl, nitro$C_{0-6}$ alkyl, hydroxy$C_{0-6}$alkyl, ($C_{0-6}$alkyl)($C_{0-6}$alkyl)amino$C_{0-6}$alkyl, ($C_{0-6}$alkyl)($C_{0-6}$alkyl)amino($C_{1-6}$ alkyl)amino$C_{0-6}$alkyl, acylamino$C_{0-6}$alkylamino, acyl$C_{0-6}$ alkyl, ($C_{0-6}$alkyl)($C_{0-6}$alkyl)aminoacyl, substituted acyl, guanidino$C_{0-6}$alkyl, hydroxyimino$C_{0-6}$alkyl, acylamino$C_{0-6}$alkyl, optionally substituted acylamino, optionally substituted acyloxy$C_{0-6}$alkyl, optionally substituted ar$C_{0-6}$alkyl, optionally substituted heteroaryl$C_{0-6}$alkyl, optionally substituted heterocyclyl$C_{0-6}$ alkyl, cyanoamino$C_{0-6}$alkyl, $C_{0-6}$alkylhydrazino, heterocyclylamino, ar$C_{0-6}$alkylhydrazino, alkylsulfonyl$C_{0-6}$alkyl, ar$C_{0-6}$alkylsulfonyl$C_{0-6}$ alkyl, alkylsulfinyl$C_{0-6}$alkyl, alkylsulfonamido$C_{0-6}$ alkyl, ar$C_{0-6}$alkylsulfonamido$C_{0-6}$alkyl, amino$C_{0-6}$ alkylsulfonyl, $C_{0-6}$alkylaminosulfonyl, acyl$C_{1-6}$ alkylsulfonyl, heterocyclylsulfonyl, amino$C_{0-6}$ alkylsulfinyl, acyl$C_{1-6}$alkylsulfinyl, silyl, siloxy, alkenoxy, alkynoxy, $C_{2-6}$alkenyl, acyl$C_{2-6}$alkenyl, $C_{2-6}$alkynyl, acyl$C_{2-6}$alkynyl, hydroxy$C_{2-6}$alkynyl, amino$C_{2-6}$alkynyl, $C_{1-6}$alkoxy$C_{0-6}$ alkyl, $C_{1-6}$alkylthio$C_{0-6}$alkyl, hydroxy$C_{1-6}$alkoxy$C_{0-6}$ alkyl, hydroxy$C_{1-6}$alkylthio$C_{0-6}$alkyl, acyl$C_{1-6}$ alkoxy$C_{0-6}$alkyl, acyl$C_{1-6}$alkylthio$C_{0-6}$alkyl, $C_{0-6}$alkylamino$C_{1-6}$alkoxy$C_{0-6}$ alkyl, $C_{0-6}$alkylamino$C_{1-6}$alkylthio$C_{0-6}$alkyl, acylamino$C_{1-6}$alkoxy$C_{0-6}$ alkyl, acylamino$C_{1-6}$alkylthio$C_{0-6}$ alkyl, ar$C_{0-6}$alkylamino$C_{0-6}$alkyl, ar$C_{0-6}$alkylthio$C_{0-6}$ alkyl, ar$C_{0-6}$ alkoxy$C_{0-6}$alkyl, ar$C_{0-6}$alkylamino, ar$C_{0-6}$ alkylamino$C_{0-6}$alkyl, ar$C_{0-6}$alkylthio, optionally substituted ar$C_{0-6}$alkoxy, optionally substituted ar$C_{0-6}$ alkylthio, or optionally substituted ar$C_{0-6}$alkoxy; and $R^5$ is $C_{0-6}$alkyl, $C_{1-6}$alkoxy$C_{1-6}$alkyl, $C_{1-6}$alkylthio$C_{1-6}$ alkyl, $C_{0-6}$alkylamino$C_{1-6}$alkyl, ar$C_{0-6}$alkyl;

provided that the compound is not 2,2,2-trifluoroethyl N'-cyano-N-{4-[({3-[(quinolin-4-ylmethyl)amino]thien-2-yl}carbonyl)amino]phenyl}-imidocarbamate;

2,2,2-trifluoroethyl N-{2-chloro-5-[({3-[(quinolin-4-ylmethyl)amino]thien-2-yl}carbonyl)amino]phenyl}-N'-cyanoimidocarbamate; or N-{1-[(cyanoimino)(dimethylamino)methyl]-2,3-dihydro-1H-indol-6-yl}-3-((quinolin-4-ylmethyl)amino)thiophene-2-carboxamide;

or a pharmaceutically acceptable salt thereof.

2. The compound, salt, or N-oxide of claim 1 wherein J is —$NR^1R^2$.

3. The compound, salt, or N-oxide of claim 2 wherein Y is optionally substituted with 1-4 independent $R^{31}$ substituents.

4. The compound, salt, of claim 1 wherein J is —$OR^1$ or —$SR^1$.

5. A pharmaceutical composition comprising a compound, or salt of claim 1 and a pharmaceutically acceptable carrier.

6. A composition comprising a compound, or salt of claim 1 and an anti-neoplastic, anti-tumor, anti-angiogenic, or chemotherapeutic agent.

7. A composition comprising a compound, or salt of claim 1 and a cytotoxic cancer therapeutic agent.

8. A composition comprising a compound, or salt of claim 1 and an angiogenesis inhibiting cancer therapeutic agent.

* * * * *